(12) United States Patent
Kondoh et al.

(10) Patent No.: US 7,416,824 B2
(45) Date of Patent: Aug. 26, 2008

(54) ORGANIC PHOTOCONDUCTIVE MATERIAL ELECTROPHOTOGRAPHIC PHOTORECEPTOR AND IMAGE FORMING APPARATUS USING THE SAME

(75) Inventors: Akihiro Kondoh, Nara (JP); Takatsugu Obata, Nara (JP); Kazuya Ishida, Souraku-gun (JP)

(73) Assignee: Sharp Kabushiki Kaisha, Osaka (JP)

( * ) Notice: Subject to any disclaimer, the term of this patent is extended or adjusted under 35 U.S.C. 154(b) by 274 days.

(21) Appl. No.: 10/556,403

(22) PCT Filed: May 10, 2004

(86) PCT No.: PCT/JP2004/006590

§ 371 (c)(1),
(2), (4) Date: Nov. 10, 2005

(87) PCT Pub. No.: WO2004/099880

PCT Pub. Date: Nov. 18, 2004

(65) Prior Publication Data

US 2006/0204871 A1 Sep. 14, 2006

(30) Foreign Application Priority Data

May 12, 2003 (JP) .............................. 2003-133352

(51) Int. Cl.
*G03G 5/047* (2006.01)
(52) U.S. Cl. .................. 430/58.85; 430/58.65; 430/72; 430/73; 564/323; 399/159
(58) Field of Classification Search .................. 430/72, 430/73, 74, 75, 76, 77, 58.65, 58.85; 399/159; 564/323
See application file for complete search history.

(56) References Cited

U.S. PATENT DOCUMENTS

| 4,123,269 A | 10/1978 | Von Hoene et al. |
| 4,150,987 A | 4/1979 | Anderson et al. |

FOREIGN PATENT DOCUMENTS

| JP | 52-4188 A | 2/1977 |
| JP | 54-150128 A | 11/1979 |
| JP | 54-151955 A | 11/1979 |
| JP | 55-52063 A | 4/1980 |
| JP | 55-42380 B2 | 10/1980 |
| JP | 58-32372 B2 | 7/1983 |
| JP | 58-198043 A | 11/1983 |
| JP | 2-51162 A | 2/1990 |
| JP | 2-184857 A | 7/1990 |
| JP | 2-190862 A | 7/1990 |
| JP | 4-120556 A | 4/1992 |
| JP | 6-43674 A | 2/1994 |
| JP | 7-48324 A | 2/1995 |
| JP | 8-95474 A | 4/1996 |
| JP | 10-69107 A | 3/1998 |
| JP | 10-239875 A | 9/1998 |
| JP | 10-254153 A | 9/1998 |
| JP | 10-260541 A | 9/1998 |
| JP | 10239875 A * | 9/1998 |
| JP | 2000112157 A * | 4/2000 |
| JP | 2002-23396 A | 1/2002 |
| JP | 2003-176276 A | 6/2003 |
| JP | 2004-287216 A | 10/2004 |
| JP | 2004-354663 A | 12/2004 |

OTHER PUBLICATIONS

Diamond, Arthur S & David Weiss (eds.) Handbook of Imaging Materials, 2nd ed.. New York: Marcel-Dekker, Inc. (Nov. 2001) pp. 145-164.*
English Translation of the International Preliminary Report on Patentability mailed Mar. 23, 2006 in corresponding PCT application No. PCT/JP2004/006590.
International Search Report of PCT/JP2004/006590, mailed Jul. 27, 2004.

* cited by examiner

*Primary Examiner*—Christopher RoDee
(74) *Attorney, Agent, or Firm*—Nixon & Vanderhye P.C.

(57) ABSTRACT

According to the present invention, an enamine compound having a specific structure is used as an organic photoconductive material. This enamine compound is obtained based on asymmetrical secondary naphtylamine which is readily available at a lowest price, by introducing phenyl groups containing substituents, as constituents units of the enamine part and presents excellent compatibility with binder resins, will not present detrimental effects such as partial crystallization at film forming and have a high charge mobility. The compound is able to realize highly reliable electrophotographic photoreceptor and an image forming apparatus which present a high electrostatic potential, high sensitivity and high enough light response and are excellent in durability and will not degrade in these characteristics under a low-temperature environment or in a high-speed process and will not lower in these characteristics even due to exposure to light.

13 Claims, 7 Drawing Sheets

Enlarged spectrum from 110 ppm to 150 ppm, shown in FIG. 6

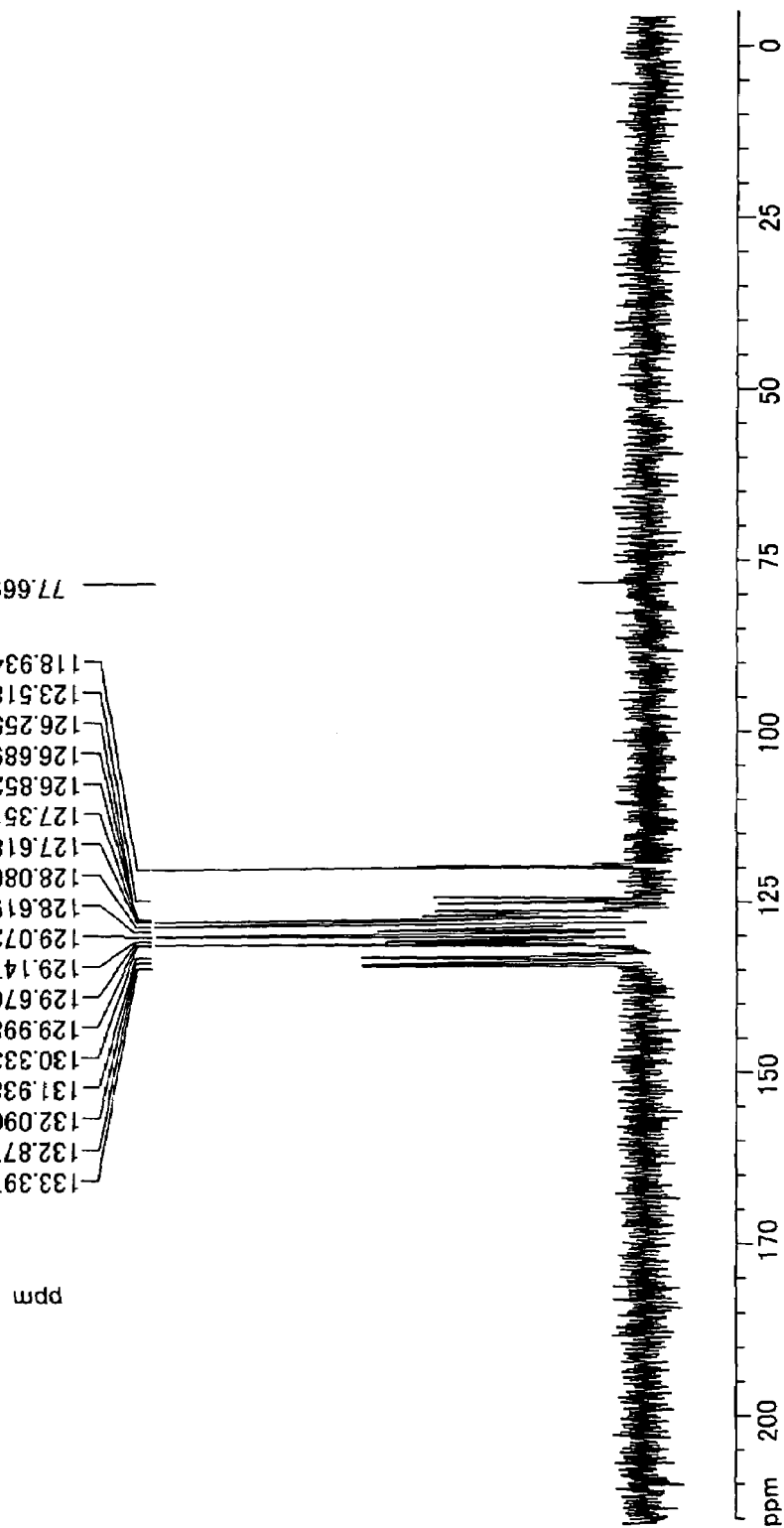

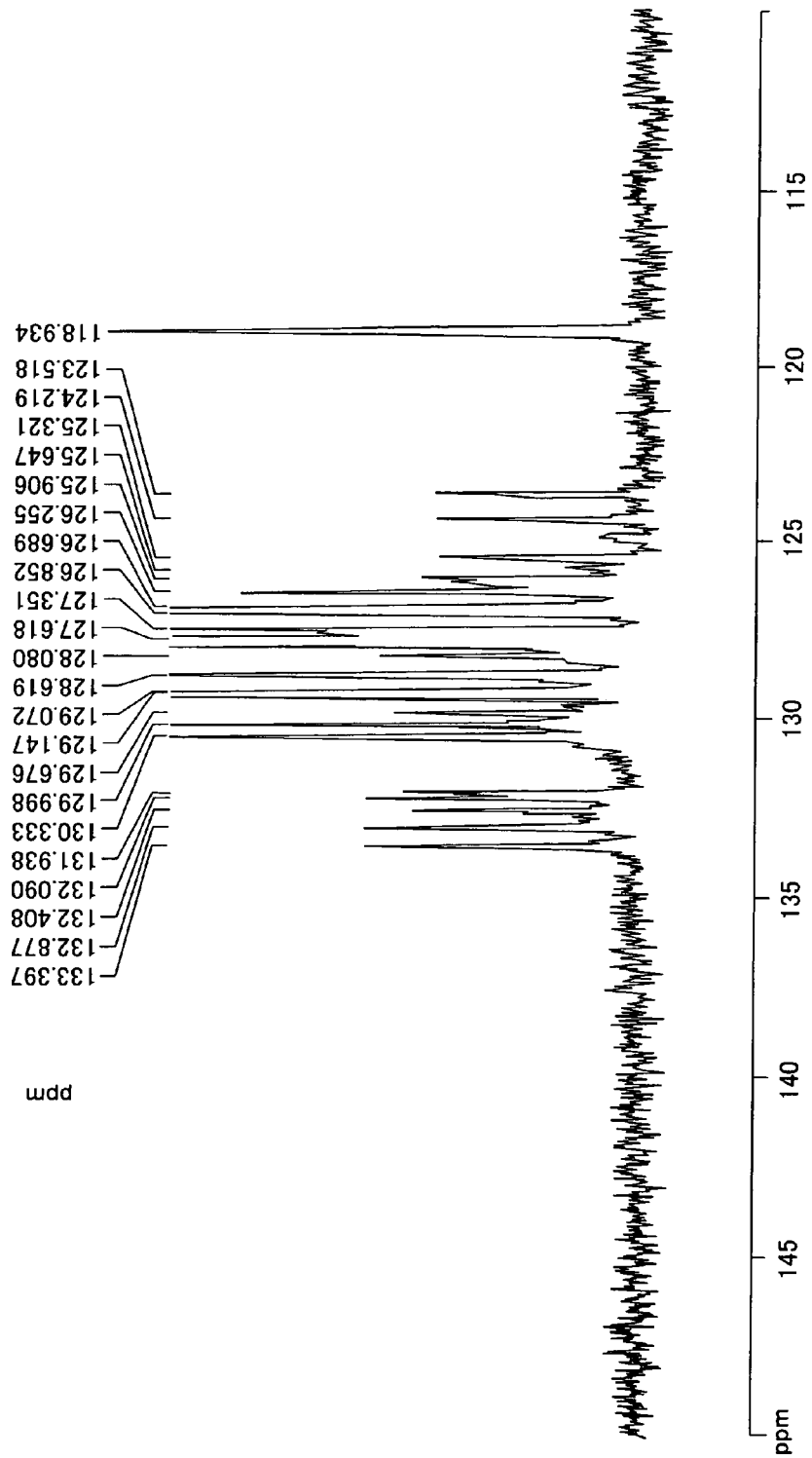

ORGANIC PHOTOCONDUCTIVE MATERIAL ELECTROPHOTOGRAPHIC PHOTORECEPTOR AND IMAGE FORMING APPARATUS USING THE SAME

This application is the US national phase of international application PCT/JP2004/006590, filed 10 May 2004, which designated the U.S. and claims priority of JP 2003-133352, filed 12 May 2003, the entire contents of each of which are hereby incorporated by reference.

TECHNICAL FIELD

The present invention relates to an organic photoconductive material and an electrophotographic photoreceptor and image forming apparatus using it.

BACKGROUND ART

Recently, organic photoconductive materials have been widely studied and developed so as to be used not only for electrophotographic photoreceptors (which will be also referred to merely as "photoreceptors") but also applied to organic electro luminescent (abbreviation: EL) devices etc. Further, the electrophotographic photoreceptors using organic photoconductive material are not limited to the field of copiers, but are also used in the fields of printing plates, slide film and microfilm in which photographic technology was previously employed. Further, they are also applied to high-speed printers which use laser, light emitting diode (abbreviation: LED), cathode ray tube (abbreviation: CRT) or the like as a light source. This means that there are high and wide demands for organic photoconductive material and electrophotographic photoreceptors using it.

Conventionally, inorganic photoreceptors having photosensitive layers mainly composed of inorganic photoconductive materials such selenium, zinc oxide, cadmium and the like have been widely used as electrophotographic photoreceptors. Though the inorganic photoreceptor has basic characteristics to some degree as a photoreceptor, it involves problems such as difficulties in forming a photosensitive layer, poor plasticity, high manufacturing cost and the like. Further, inorganic photoconductive materials generally have strong toxicity, hence a severe restriction is imposed when they are handled and used for manufacturing.

In contrast, the organic photoreceptor using organic photoconductive material exhibits good performance in film-forming of photosensitive layers, is excellent in flexibility, lightweight and highly transparent. Further, since the organic photoreceptor has advantages such as that it can be readily designed so as to present excellent sensitivity for a wide wavelength range by an appropriate sensitization process, it has gradually come to play the leading role in the development of electrophotographic photoreceptors. The initial organic photoreceptors had sensitivity and durability drawbacks, but these drawbacks have been markedly improved by the development of a function-separation type electrophotographic photoreceptor in which the function of charge generation and the function of charge transport are allotted to different substances. The function-separation type photoreceptor is advantageous in presenting a wide selection of materials for charge generation material providing the function of charge generation and for charge transport material providing the function of charge transport and in enabling relatively easy fabrication of electrophotographic photoreceptors having arbitrary characteristics.

As the charge generation material to be used for such a function-separation type photoreceptor, many kinds of substances such as phthalocyanine pigments, squarylium dyes, azo pigments, perylene pigments, polycyclic quinone pigments, cyanine dyes, squaric acid dyes, pyrylium salt dyes, etc., have been investigated, and various kinds of substances having strong light resistance and high charge generation capability have been proposed.

On the other hand, as the charge transport material, various compounds such as pyrazoline compounds (c.f. Japanese Patent Publication No. Sho 52-4188), hydrazone compounds (c.f. Japanese Patent Application Laid-open No. Sho 54-150128, Japanese Patent Publication No. Sho 55-42380 and Japanese Patent Application Laid-open No. Sho 55-52063), triphenyl amine compounds (c.f. Japanese Patent Publication No. Sho 58-32372 and Japanese Patent Application Laid-open No. Hei 02-190862), and stilbene compounds (c.f. Japanese Patent Application Laid-open No. Sho 54-151955 and Japanese Patent Application Laid-open No. Sho 58-198043), are known. In recent years, pyrene derivatives, naphthalene derivatives, terphenyl derivatives (c.f. Japanese Patent Application Laid-open No. Hei 07-48324) and the like, having condensed polycyclic hydrocarbons as a central parent nucleus, have been developed.

The charge transport material is required:
(1) to be stable to light and heat;
(2) to be stable to ozone, nitrogen oxides ($NO_x$) and nitric acid etc., which arise during corona discharge for charging the photoreceptor surface;
(3) to have a high charge transport capability;
(4) to have a high compatibility with organic solvents and binders; and
(5) to be easy to produce and inexpensive.

However, the aforementioned charge transport materials satisfy part of these requirements but have yet to meet all these requirements to high levels.

Further, of the above requirements, the charge transport material is particularly required to have a high charge transport capability. For example, when a charge transport layer of the charge transport material dispersed with the binder resin forms the surface layer of the photoreceptor, the charge transport material is required to have a high charge transport capability in order to secure a high enough light response. When the photoreceptor is provided and used for a copier, laser beam printer or the like, the photoreceptor surface layer is forced to be partially scraped off by contact members such as a cleaning blade, charging roller etc. Therefore, in order to enhance the durability of the copier or laser beam printer, a robust surface layer against these contact members, that is, a high wear-resistant surface layer which is less scraped off by the contact members is demanded. If, for this purpose, the binder resin content in the surface layer or charge transport layer is made higher in order to make the surface layer strong and durable, the light response lowers. This occurs because the charge transport capability of the charge transport material is low and the charge transport material in the charge transport layer is diluted with increase of the binder resin content. As a result, the charge transport capability of the charge transport layer is further lowered resulting in poor light response. Since degradation of the light response will cause increase in the residual surface potential and the photoreceptor will be repeatedly used without its surface potential sufficiently attenuated, the surface charge in the areas to be removed by exposure to light cannot be adequately eliminated, causing degradation of image quality and other defects at an early stage. This is why a high charge transport capability is wanted for the charge transport material in order to secure high enough light response.

Further, with the recent development of electrophotographic apparatus such as digital copiers and printers into miniaturization and high-speed configuration, high-sensitive photoreceptor characteristics are demanded to deal with a high-speed configuration. Therefore, a further increased charge transport capability is demanded for the charge transport material. Further, since the time taken from exposure to development is short in a high-speed process, photoreceptors of good light response are demanded. As stated above, since the light response depends on the charge transport capability of the charge transport material, charge transport material having a high charge transport capability is wanted from this viewpoint.

As the charge transport material that meets the above requirements, enamine compounds having a higher charge mobility than the aforementioned charge transport materials have been proposed (see Japanese Patent Application Laid-open No. Hei 02-51162, Japanese Patent Application Laid-open No. Hei 06-43674, Japanese Patent Application Laid-open No. Hei 10-69107 and Japanese Patent Application Laid-open No. Hei 10-239875).

However, the photoreceptors formed with the enamine compounds disclosed in Japanese Patent Application Laid-open No. Hei 02-51162, Japanese Patent Application Laid-open No. Hei 06-43674 and Japanese Patent Application Laid-open No. Hei 10-69107 are not effective enough. On the other hand, since the enamine compound disclosed in Japanese Patent Application Laid-open No. Hei 10-239875 presents a highly symmetric configuration when a bis-butadiene substructure is introduced, the compound will exhibit markedly bad compatibility with the binder resin, hence will present detrimental effects such as partial crystallization at film forming, etc. As a countermeasure against this problem, it is possible to make improvement to some degree by replacing the substituents of the enamine structure, from a large structural unit such as an aryl group etc., to a methyl group, the minimum structural unit. However, from a viewpoint of electric characteristics (particularly, in view of hall drift mobility), an aryl group is preferred as the substituents of the enamine structure to an alkyl group; this is the problem to overcome.

Also, the photoreceptor is wanted to have reliable characteristics, presenting little variation in characteristics under various environments without lowering its sensitivity even in a low-temperature environment. However, no charge transport material which can also realize such characteristics has been obtained so far.

DISCLOSURE OF INVENTION

The object of the present invention is to provide an organic photoconductive material capable of realizing a highly reliable electrophotographic photoreceptor which will not present detrimental effects such as partial crystallization etc., at film forming; will present a high sensitivity, sufficient light response and excellent durability; will not degrade in these characteristics even when used under a low-temperature environment or in a high-speed process and will not degrade in these characteristics due to exposure to light. Another object of the present invention is to provide an electrophotographic photoreceptor and an image forming apparatus using it.

Specifically, the present invention is characterized by the following configuration or means and is to achieve the above objects.

The present invention is an organic photoconductive material represented by the following general formula (1):

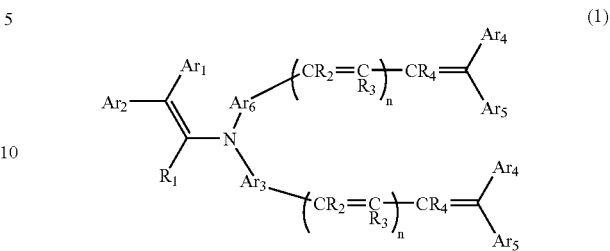

where n is an integer ranging from 0 to 3; $Ar^1$ and $Ar^2$ each represent an aryl group optionally containing a substituent or a heterocyclic group optionally containing a substituent; $Ar^3$ and $Ar^6$ each represent an arylene group optionally containing a substituent or a bivalent heterocyclic group optionally containing a substituent, with each being different from the other; $Ar^4$ and $Ar^5$ represent one selected from a hydrogen atom, aryl groups optionally containing a substituent, heterocyclic groups optionally containing a substituent, aralkyl groups optionally containing a substituent and alkyl groups optionally containing a substituent, and both $Ar^4$ and $Ar^5$ are not, at the same time, hydrogen atoms, $Ar^4$ and $Ar^5$ may be bonded to each other via an atom or an atomic group, forming a cyclic structure; $R^1$ represents a hydrogen atom, a halogen atom or an alkyl group optionally containing a substituent; and $R^2$, $R^3$ and $R^4$ are selected from a hydrogen atom, alkyl groups optionally containing a substituent, aryl groups optionally containing a substituent, heterocyclic groups optionally containing a substituent and aralkyl groups optionally containing a substituent, and if there are multiple identical notations, they may be the same with or different from each other, and when n is 0, $Ar^3$ is limited to represent a heterocyclic group optionally containing a substituent.

According to the present invention, since the organic photoconductive material is an enamine compound represented by the above general formula (1), it has a high charge mobility. Further, in order to break the symmetry of the molecular structure, sub structures ($Ar^3$, $Ar^6$), each intentionally being differentiated from the other, are built in at an early stage of synthesis, hence the material presents excellent compatibility with binder resins, having a high charge mobility that will not cause any detrimental effects such as partial crystallization etc., at film forming. In the present invention, it is possible to use such an organic photoconductive material as a charge transport material. This makes it possible to realize a highly reliable electrophotographic photoreceptor which presents a high electrostatic potential, high sensitivity and high enough light response as well as excellent durability and will not degrade in these characteristics under a low-temperature environment or in a high-speed process and will not lower in these characteristics even due to exposure to light. Further, application of the organic photoconductive material to sensor materials, EL devices, electrostatic recording devices and the like will be able to provide devices that are excellent in response.

Further, the present invention is characterized in that the organic photoconductive material represented by the above general formula (1) is one represented by the following general

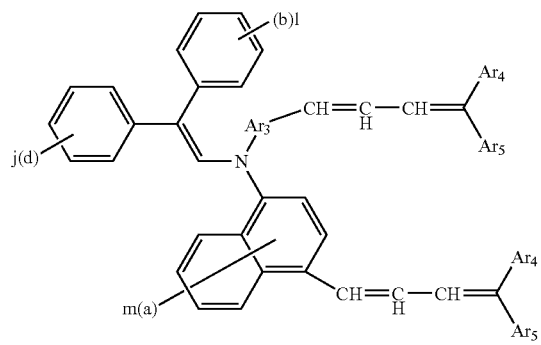

(2)

where j and l each are an integer ranging from 1 to 5, m is an integer ranging from 1 to 6; a, b and d each represent one selected from alkyl groups optionally containing a substituent, alkoxy groups optionally containing a substituent, dialkylamino groups optionally containing a substituent, aryl groups optionally containing a substituent, halogen atoms and a hydrogen atom, and when a, b and d each appear in plurality, they may be the same with or different from each other, and also may be joined to each other forming a cyclic structure.

According to the present invention, the organic photoconductive material represented by the above general formula (1), particularly the enamine compound represented by the above general formula (2), can be obtained based on asymmetrical secondary naphtylamine which is readily available at a lowest price, by introducing phenyl groups containing substituents, as constituent units of the enamine part. It is therefore possible to readily obtain an organic photoconductive material that presents excellent compatibility with binder resins, will not present detrimental effects such as partial crystallization etc., at film forming, and have a high charge mobility. In this way use of such an organic photoconductive material having an especially high charge mobility as a charge transport material makes it possible to provide an electrophotographic photoreceptor that presents a high electrostatic potential, high sensitivity and high enough light response. It is also possible to realize a highly reliable electrophotographic photoreceptor which presents excellent durability and will not degrade in these characteristics under a low-temperature environment or in a high-speed process and will not lower in these characteristics even due to exposure to light. Further, application of the organic photoconductive material to sensor materials, EL devices, electrostatic recording devices and the like will be able to provide devices that are excellent in response.

Further in an electrophotographic photoreceptor comprising: a conductive substrate consisting of a conductive material; and a photosensitive layer containing a charge generation material and a charge transport material and provided on the conductive substrate, it is characterized that the charge transport material contains the aforementioned organic photoconductive material.

According to the present invention, since the photosensitive layer contains as a charge transport material an organic photoconductive material having a high mobility, represented by the above general formula (1), specifically by (2), it is possible to obtain a highly reliable electrophotographic photoreceptor which presents a high electrified potential, high sensitivity and high enough light response as well as excellent durability and will not degrade in these characteristics under a low-temperature environment or in a high-speed process. Further, since the photosensitive layer is able to achieve a high charge transport capability without any content of polysilane, it is possible to obtain a highly reliable electrophotographic photoreceptor which will not lower in the characteristics due to exposure to light.

The present invention is also characterized in that the charge generation material contains oxotitanium phthalocyanine.

According to the present invention, the photosensitive layer contains as a charge generation material oxotitanium phthalocyanine that at least presents a clear diffraction peak at a Bragg angle ($2\theta \pm 0.2°$) of $27.2°$ in a X-ray diffraction spectrum with a Cu—K$\alpha$ characteristic X-ray (wavelength: 1.54 Å). The oxotitanium phthalocyanine that at least presents a clear diffraction peak at a Bragg angle ($2\theta \pm 0.2°$) of $27.2°$ in a X-ray diffraction spectrum with a Cu—K$\alpha$ characteristic X-ray (wavelength: 1.54 Å) has high charge generation efficiency and charge injection efficiency. This charge transport material generates a large quantity of charge as it absorbs light and efficiently injects electric charge into the charge transport material without accumulating the generated charge therein. Further, as stated above, the photosensitive layer contains as a charge transport material an organic photoconductive material having a high mobility, represented by the above general formula (1), specifically by (2). Accordingly, electric charge generated from the charge generation material by light absorption is efficiently injected into the charge transport material and smoothly transported thereby, hence it is possible to provide an electrophotographic photoreceptor having a high sensitivity and a high resolution.

Also, the photosensitive layer is characterized in that by having a layered structure composed of a charge generation layer containing the charge generation material and a charge transport layer containing the charge transport material.

According to the present invention, the photosensitive layer has a layered structure composed of a charge generation layer containing a charge generation material and a charge transport layer containing a charge transport material. Since the charge generation function and the charge transport function are assigned to different layers in the above way, it is possible to select optimal materials for the function of charge generation and the function of charge transport, respectively. As a result, it is possible to obtain an electrophotographic photoreceptor presenting a higher sensitivity and increased stability and high durability against repeated usage.

Also, the charge transport layer is characterized in that it further contains a binder resin, and in the charge transport layer the ratio A/B of the charge transport material (A) and the binder resin (B) ranges from 10/12 to 10/30 in mass ratio.

According to the present invention, the ratio A/B of the charge transport material (A) and the binder resin (B) contained in the charge transport layer ranges from ten twelfths (10/12) to ten thirtieths (10/30) in mass ratio. As described above, since the charge transport material contains the organic photoconductive material of the present invention which has a high charge mobility, it is possible to maintain the light response even if the binder is added at a ratio, specifically, the aforementioned ratio A/B is set at 10/12 to 10/30, which is higher than that for the conventionally known charge transport material. Accordingly, it is possible to improve the abrasion resistance of the charge transport layer and improve the durability of the electrophotographic photoreceptor without degradation of light response.

The present invention is also characterized in that an intermediate layer is formed between the conductive substrate and the photosensitive layer.

According to the present invention, an intermediate layer is formed between the conductive substrate and the photosensitive layer. Since this makes it possible to prevent injection of electric charge from the conductive substrate into the photosensitive layer, it is possible to prevent lowering of the electrification capability of the photosensitive layer, hence inhibit reduction of the surface charge in the areas other than that to be erased by exposure to light and prevent defects such as image fogging etc. from occurring. Since this also makes it possible to form the conductive substrate surface uniform by covering the defects on that surface, it is possible to enhance the film formability of the photosensitive layer. It is also possible to prevent the photosensitive layer from peeling from the conductive substrate and enhance the adhesiveness between the conductive substrate and the photosensitive layer.

Further, the present invention is an image forming apparatus including the above electrophotographic photoreceptor.

According to the present invention, since it is possible to obtain a highly reliable electrophotographic photoreceptor which can present a high electrified potential, high sensitivity and high enough light response as well as excellent durability and will not degrade in these characteristics under a low-temperature environment or in a high-speed process, it is possible to provide an highly reliable image forming apparatus which can present high-quality images under various environments. Also, since the electrophotographic photoreceptor will not degrade in the characteristics by exposure to light, it is possible to prevent the image quality degradation as a result of the photoreceptor being exposed to light during maintenance and the like and hence improve the reliability of the image forming apparatus.

BRIEF DESCRIPTION OF DRAWINGS

FIG. 8 is a chart of a $^{13}$C-NMR spectrum, measured by DEPT135, of an example compound No. 28(1-1) of the present embodiment.

FIG. 9 is a chart showing the enlarged spectrum from 110 ppm to 150 ppm of the chart shown in FIG. 8.

BEST MODE FOR CARRYING OUT THE INVENTION

Figure 1:
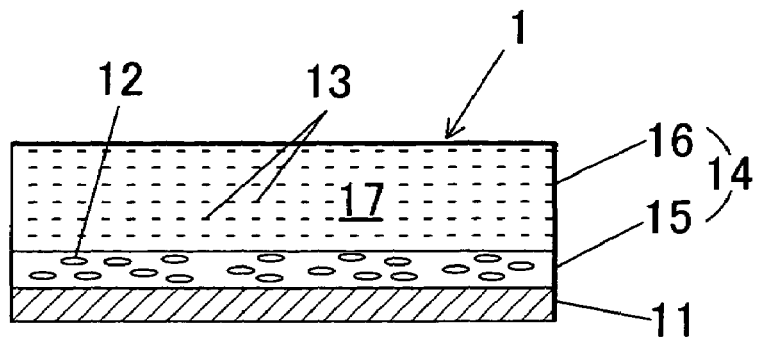
FIG. 1 is a simplified schematic sectional view showing an electrophotographic photoreceptor as one example of the present embodiment mode.

The embodiment modes of the present invention will be described in detail with reference to the drawings.

The organic photoconductive material of the present invention is an enamine compound represented by the following general formula (1):

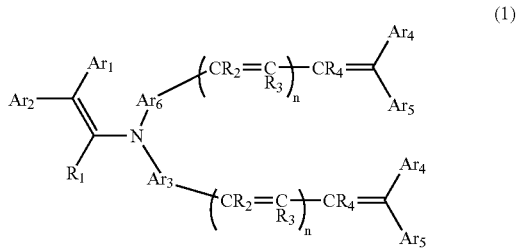

In the above general formula (1), $Ar^1$ and $Ar^2$ each represent an aryl group optionally containing a substituent or a heterocyclic group optionally containing a substituent. Specific examples of $Ar^1$ and $Ar^2$ include aryl groups such as phenyl, tolyl, methoxyphenyl, naphthyl, biphenylyl and the like, and heterocyclic groups such as furyl, thienyl, thiazolyl, benzofuryl and N-methyl-indolyl and the like.

In the above general formula (1), $Ar^3$ and $Ar^6$ each represent an arylene group optionally containing a substituent or a bivalent heterocyclic group optionally containing a substituent, with each being different from the other.

Specific examples of $Ar^3$ and $Ar^6$ include: aryl groups such as p-phenylene, m-phenylene, methyl-p-phenylene, methoxy-p-phenylene, α-naphthylene, β-naphthylene, pyrenylene, biphenylene, phenoxyphenylene, phenylthio phenylene and the like; and heterocyclic groups such as 1,4-furyl, 1,4-thienyl, 1,4-thiazolyl, 2,5-benzofuryl, 2,5-benzothiophenyl, 2,5-N-methylindolyl, 2,5-benzothiazolyl, 2,5-benzooxazolyl, 3,6-N-ethylcarbazolyl and the like.

In the above general formula (1), $Ar^4$ and $Ar^5$ represent one selected from a hydrogen atom, aryl groups optionally containing a substituent, heterocyclic groups optionally containing a substituent, aralkyl groups optionally containing a substituent and alkyl groups optionally containing a substituent. Here, however, both $Ar^4$ and $Ar^5$ are not, at the same time, hydrogen atoms.

Specific examples of $Ar^4$ and $Ar^5$ may include: other than a hydrogen atom, aryl groups such as phenyl, tolyl, methoxyphenyl, naphthyl, pyrenyl, biphenylyl, phenoxyphenyl, p-(phenylthio)phenyl, p-styrylphenyl and the like; heterocyclic groups such as furyl, thienyl, thiazolyl, benzofuryl, benzothiophenyl, N-methyl indolyl, benzothiazolyl, benzooxazolyl, N-ethylcarbazolyl and the like; aralkyl groups such as benzyl, p-methoxybenzyl, 1-naphthylmethyl and the like; alkyl groups such as methyl, ethyl, trifluoromethyl, fluoromethyl, isopropyl, t-butyl, cyclohexyl, cyclopentyl, 2-thienylmethyl and the like.

$Ar^4$ and $Ar^5$ may be bonded to each other via an atom or an atomic group, forming a cyclic structure.

Specific examples of atoms for bonding $Ar^4$ and $Ar^5$ may include an oxygen atom and a sulfur atom. Specific examples of atomic groups for bonding $Ar^4$ and $Ar^5$ may include bivalent atomic groups such as nitrogen atoms having an alkyl. Further, bivalent atomic groups for bonding $Ar^4$ and $Ar^5$ may include alkylene groups such as methylene, ethylene, methylethylene, etc.; unsaturated alkylene groups such as vinylene, propenylene etc.; heteroatom-containing alkylene groups such as oxymethylene (chemical formula: —O—CH$_2$—) and the like and; unsaturated heteroatom-containing alkylene groups such as thio-vinylene (chemical formula: —S—CH═CH—) and other bivalent groups.

In the above general formula (1), $R^1$ represents a hydrogen atom, a halogen atom or an alkyl group optionally containing a substituent. Specific examples of $R^1$ may include: other than hydrogen atom, alkyl groups such as methyl, ethyl, n-propyl, isopropyl, trifluoromethyl etc. and halogen atoms such as fluorine atom, chlorine atom etc.

In the above general formula (1), $R^2$, $R^3$ and $R^4$ are selected from a hydrogen atom, alkyl groups optionally containing a substituent, aryl groups optionally containing a substituent, heterocyclic groups optionally containing a substituent and aralkyl groups optionally containing a substituent. Specific examples of $R^2$, $R^3$ and $R^4$ may include: other than hydrogen atom, alkyl groups such as methyl, ethyl, n-propyl, isopropyl, trifluoromethyl, 2-thienylmethyl etc.; aryl groups such as phenyl, tolyl, methoxyphenyl, naphthyl etc.; heterocyclic groups such as furyl, thienyl, thiazolyl etc. and; aralkyl groups such as benzyl, p-methoxybenzyl etc.

Additionally, when the above general formula (1) includes two or more of $R^2$, $R^3$ or $R^4$, they may be the same group or different groups as long as they are those listed above.

In the above general formula (1), n represents an integer from 0 to 3, and when n is 0, $Ar^3$ is limited to represent a heterocyclic group optionally containing a substituent.

Since the organic photoconductive material of the present invention is an enamine compound denoted by the above general formula (1), it has high charge mobility. Thus, use of an organic photoconductive material having a high charge mobility of the present invention as a charge transport material realizes a highly reliable electrophotographic photoreceptor which presents a high electrified potential, high sensitivity and high enough light response as well as excellent durability and will not degrade in these characteristics under a low-temperature environment or in a high-speed process and will not lower in these characteristics even due to exposure to light. Further, application of the organic photoconductive material to sensor materials, EL devices, electrostatic recording devices and the like will provide devices that are excellent in response.

Among the organic photoconductive materials shown in the above general formula (1), enamine compounds shown in the following general formula (2) can be recommended as preferable compounds.

The substituents designated by a, b or d are any of an alkyl group optionally containing a substituent, alkoxy group optionally containing a substituent, a dialkylamino group optionally containing a substituent, an aryl group optionally containing a substituent and a halogen atom. Further, the groups listed above for a, b and d each may have a structure of a bivalent or higher-valent group such as diyl, irene or the like, forming a cyclic structure by boding to each other. When two or more are shown in the above general formula (2), the groups may be the same with or different from each other as long as they are those listed above.

Specific examples of a, b and d may include hydrogen atom; alkyl groups such as methyl, ethyl, n-propyl, isopropyl, trifluoromethyl, fluoromethyl, 1-methoxyethyl etc.; alkoxy groups such as methoxy, ethoxy, n-propoxy, isopropoxy etc.; dialkylamino groups such as dimethylamino, diethylamino, diisopropylamino etc.; aryl groups such as phenyl, tolyl, methoxyphenyl, naphthyl etc. and; halogen atoms such as fluorine atom, chlorine atom etc.

The enamine compounds represented by the above general formula (2) present particularly high charge mobility, and can be produced easily. Accordingly, when the organic photoconductive material represented by the above general formula (1) is an enamine compound specified by the above general formula (2), it is possible to easily obtain an organic photoconductive material having a particularly high charge mobility.

Recommended as excellent compounds, in view of the characteristics, cost and productivity etc., from the organic photoconductive materials shown by the above general formula (1), can be those where $Ar^1$ and $Ar^2$ are phenyls, $Ar^3$ is α-naphthyl, $Ar^6$ is p-phenylene, methyl-p-phenylene, methoxy-p-phenylene, 1,4-biphenylene, or 1,4-thienyl, at least one of $Ar^4$ and $Ar^5$ is phenyl, p-tolyl, p-methoxyphenyl, naphthyl, thienyl or thiazolyl, $R^1$, $R^2$, $R^3$ and $R^4$ are all hydrogen atoms and n is 1.

As the specific examples of the organic photoconductive materials of the present invention shown by the above general formula (1), example compounds having the groups shown in the following Tables 1 to 16 can be listed for instance. However, the organic photoconductive material of the present invention should not be limited to these. The groups shown in Table 1 correspond to those shown in the above general formula (1).

For example, example compound No. 28 shown in Table 6 below is an enamine compound that is represented by the following constitutional formula (1-1).

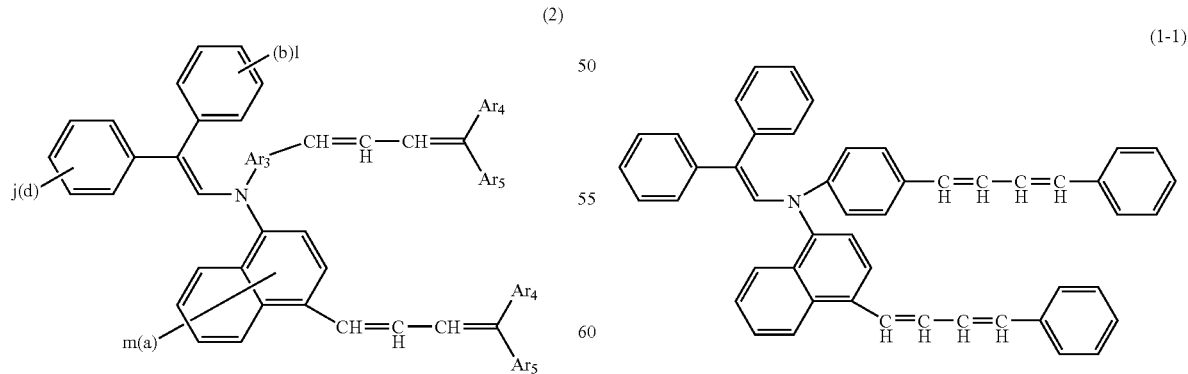

In the above general formula (2), j, m and 1 denote the numbers of substituents while a, b and d represent the types of the substituents. Here, m ranges from 1 to 6 and j and 1 range from 1 to 5.

For those which form a cyclic structure with $Ar^4$ and $Ar^5$ bonded to each other, the cells for $Ar^4$ and $Ar^5$ are joined so that the C—C double bond formed with $Ar^4$ and $Ar^5$ and the cyclic structure formed by the carbon atom of the C—C double bond and $Ar^4$ and $Ar^5$ can be shown together.

TABLE 1

| Example Compound No. | Ar¹ | Ar² | R¹ | N—Ar³ | N—Ar⁶ | n | CR²=CR³ | R⁴ | Ar⁴ | Ar⁵ |
|---|---|---|---|---|---|---|---|---|---|---|
| 1 | phenyl | phenyl | H | p-phenylene | 1,4-naphthylene | 1 | CH=CH | H | phenyl | phenyl |
| 2 | phenyl | phenyl | H | p-phenylene | 1,4-naphthylene | 1 | CH=CH | H | H | 4-CH₃-phenyl |
| 3 | phenyl | phenyl | H | p-phenylene | 1,4-naphthylene | 1 | CH=CH | H | —CH₃ | 4-OCH₃-phenyl |
| 4 | phenyl | phenyl | H | p-phenylene | 1,4-naphthylene | 1 | CH=CH | H | H | 4-N(CH₃)₂-phenyl |
| 5 | phenyl | phenyl | H | p-phenylene | 1,4-naphthylene | 1 | CH=CH | H | H | 4-CH(CH₃)₂-phenyl |

TABLE 2

| Example Compound No. | Ar¹ | Ar² | R¹ | N—Ar³ | N—Ar⁶ | n | CR²=CR³ | R⁴ | Ar⁴ | Ar⁵ |
|---|---|---|---|---|---|---|---|---|---|---|
| 6 | phenyl | 4-methylphenyl | H | 4-aminophenyl | 1-amino-4-methylnaphthyl | 1 | CH=CH | H | H | 4-chloro-methylphenyl |
| 7 | phenyl | 4-methylphenyl | H | 4-aminophenyl | 1-amino-4-methylnaphthyl | 1 | CH=CH | H | —CH₃ | 3-methylphenyl |
| 8 | phenyl | 4-methylphenyl | H | 4-aminophenyl | 1-amino-4-methylnaphthyl | 1 | CH=CH | H | H | 2-fluoro-methylphenyl |
| 9 | phenyl | 4-methylphenyl | H | 4-aminophenyl | 1-amino-4-methylnaphthyl | 1 | CH=CH | H | —CH₃ | 4-(CH₂CH₂F)phenyl |
| 10 | phenyl | 4-methylphenyl | H | 4-aminophenyl | 1-amino-4-methylnaphthyl | 1 | CH=CH | H | —CH₃ | 3,5-dimethyl-4-methyl-(OCH₃)phenyl |

TABLE 3

| Example Compound No. | Ar¹ | Ar² | R¹ | N—Ar³ | N—Ar⁶ | n | CR²=CR³ | R⁴ | Ar⁴ | Ar⁵ |
|---|---|---|---|---|---|---|---|---|---|---|
| 11 | phenyl | phenyl | H | p-phenylene | 4-methyl-1-naphthyl | 1 | CH=CH | H | H | 5-methyl-1,2,3,4-tetrahydronaphthyl |
| 12 | phenyl | phenyl | H | p-phenylene | 4-methyl-1-naphthyl | 1 | CH=CH | H | H | 6-methylchroman-yl |
| 13 | phenyl | phenyl | H | p-phenylene | 4-methyl-1-naphthyl | 1 | CH=CH | H | H | 4'-methylbiphenyl |
| 14 | phenyl | phenyl | H | p-phenylene | 4-methyl-1-naphthyl | 1 | CH=CH | H | H | 4-(phenylthio)-phenyl-methyl |
| 15 | phenyl | phenyl | H | p-phenylene | 4-methyl-1-naphthyl | 1 | CH=CH | H | H | 4-(4-methylphenoxy)phenyl |

TABLE 4

| Example Compound No. | Ar¹ | Ar² | R¹ | N—Ar³ | N—Ar⁶ | n | CR²=CR³ | R⁴ | Ar⁴ | Ar⁵ |
|---|---|---|---|---|---|---|---|---|---|---|
| 16 | 4-methylphenyl | biphenyl | H | 1,4-phenylene | 4-methylnaphthalen-1-yl | 1 | CH=CH | H | —CH₃ | biphenyl |
| 17 | 4-methylphenyl | phenyl | H | 1,4-phenylene | 4-methylnaphthalen-1-yl | 1 | CH=CH | H | H | 4-methylstilbenyl |
| 18 | 4-methylphenyl | phenyl | H | 1,4-phenylene | 4-methylnaphthalen-1-yl | 1 | CH=CH | H | —CH₃ | naphthalen-1-yl |
| 19 | 4-methylphenyl | phenyl | H | 1,4-phenylene | 4-methylnaphthalen-1-yl | 1 | CH=CH | H | H | 4-methyl-1-methoxynaphthyl |
| 20 | 4-methylphenyl | phenyl | H | 1,4-phenylene | 4-methylnaphthalen-1-yl | 1 | CH=CH | H | H | 6-methoxy-2-methylnaphthyl |

TABLE 5
| Example Compound No. | Ar¹ | Ar² | R¹ | N—Ar³ | N—Ar⁶ | n | CR²=CR³ | R⁴ | Ar⁴ | Ar⁵ |
|---|---|---|---|---|---|---|---|---|---|---|
| 21 | 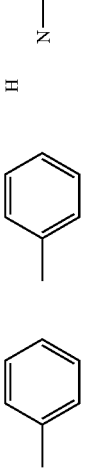 | 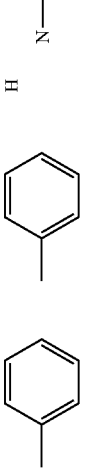 | H | 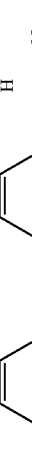 | 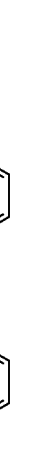 | 1 | CH=CH | H | H | 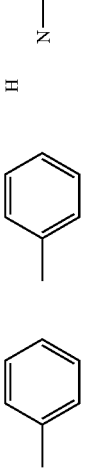 |
| 22 | 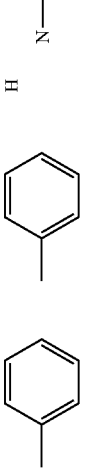 | 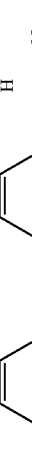 | H | 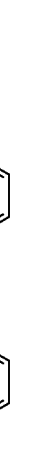 | 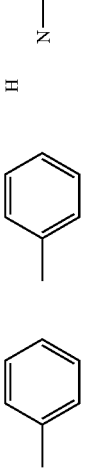 | 1 | CH=CH | H | H | 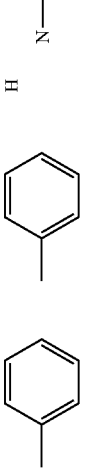 |
| 23 | 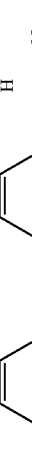 | 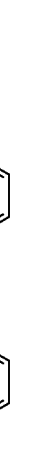 | H | 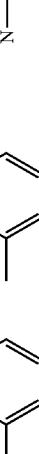 | 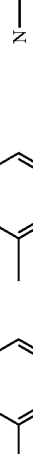 | 1 | CH=CH | H | —CH₃ | 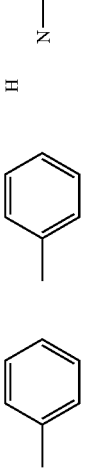 |
| 24 | 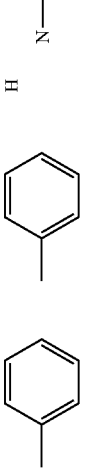 | 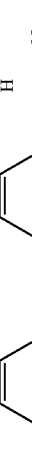 | H | 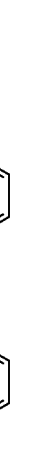 | 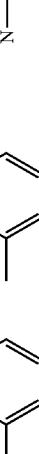 | 1 | CH=CH | H | —CH₃ | 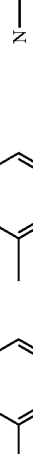 |
| 25 | 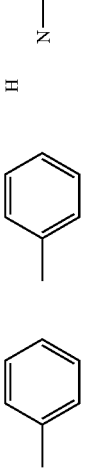 | 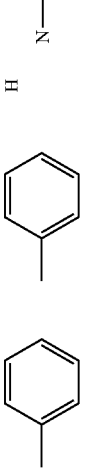 | H | 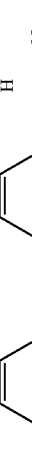 | 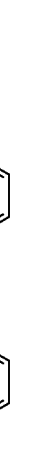 | 1 | CH=CH | H | H | 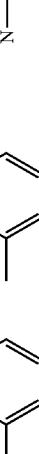 |

TABLE 6

| Example Compound No. | Ar¹ | Ar² | R¹ | N—Ar³ | N—Ar⁶ | n | CR²=CR³ | R⁴ | Ar⁴ | Ar⁵ |
|---|---|---|---|---|---|---|---|---|---|---|
| 26 | phenyl | phenyl | H | p-phenylene | 1,4-naphthylene (with methyl) | 1 | CH=CH | H | H | 2-methylbenzothiazole |
| 27 | phenyl | phenyl | H | p-phenylene | 1,4-naphthylene (with methyl) | 1 | CH=CH | H | H | 3-methyl-9-ethylcarbazole |
| 28 | phenyl | phenyl | H | p-phenylene | 1,4-naphthylene (with methyl) | 1 | CH=CH | H | H | phenyl |
| 29 | phenyl | phenyl | H | p-phenylene | 1,4-naphthylene (with methyl) | 1 | CH=CH | H | 4-CH₃-phenyl | 4-CH₃-phenyl |
| 30 | phenyl | phenyl | H | p-phenylene | 1,4-naphthylene (with methyl) | 1 | CH=CH | H | 4-OCH₃-phenyl | 4-OCH₃-phenyl |

TABLE 7

| Example Compound No. | Ar¹ | Ar² | R¹ | N—Ar³ | N—Ar⁶ | n | CR²=CR³ | R⁴ | Ar⁴ | Ar⁵ |
|---|---|---|---|---|---|---|---|---|---|---|
| 31 | 4-methylphenyl | phenyl | H | 1,4-phenylene | 4-methylnaphthalen-1-yl | 1 | CH=CH | H | 4-(N(CH₃)₂)phenyl | 4-(N(CH₃)₂)phenyl |
| 32 | 4-methylphenyl | phenyl | H | 1,4-phenylene | 4-methylnaphthalen-1-yl | 1 | CH=CH | H | phenyl | phenyl |
| 33 | 4-methylphenyl | phenyl | H | 1,4-phenylene | 4-methylnaphthalen-1-yl | 1 | CH=CH | H | phenyl | thiophen-2-yl |
| 34 | 4-methylphenyl | phenyl | H | 1,4-phenylene | 4-methylnaphthalen-1-yl | 1 | CH=CH | H | | 3,4-dihydronaphthalen-1(2H)-ylidene |
| 35 | 4-methylphenyl | phenyl | H | 1,4-phenylene | 4-methylnaphthalen-1-yl | 1 | CH=CH | H | | 10H-anthracen-9-ylidene |

TABLE 8

| Example Compound No. | Ar¹ | Ar² | R¹ | N—Ar³ | N—Ar⁶ | n | CR²=CR³ | R⁴ | Ar⁴ | Ar⁵ |
|---|---|---|---|---|---|---|---|---|---|---|
| 36 | phenyl | phenyl | H | p-phenylene | 1,4-naphthylene | 1 | CH=CH | H | | dibenzosuberylidene |
| 37 | phenyl | phenyl | H | p-phenylene | 1,4-naphthylene | 1 | CH=CH | H | | thioxanthylidene |
| 38 | phenyl | phenyl | H | p-phenylene | 1,4-naphthylene | 1 | CH=CH | H | | N-methyl-acridinylidene |
| 39 | phenyl | phenyl | H | p-phenylene | 1,4-naphthylene | 1 | CH=CH | —CH₃ | H | phenyl |
| 40 | phenyl | phenyl | H | p-phenylene | 1,4-naphthylene | 1 | CH=CH | phenyl | H | phenyl |

TABLE 9
| Example Compound No. | Ar¹ | Ar² | R¹ | N—Ar³ | N—Ar⁶ | n | CR²=CR³ | R⁴ | Ar⁴ | Ar⁵ |
|---|---|---|---|---|---|---|---|---|---|---|
| 41 | 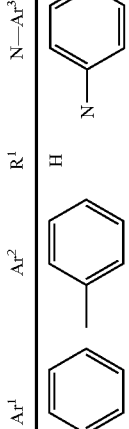 | 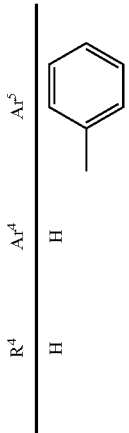 | H | 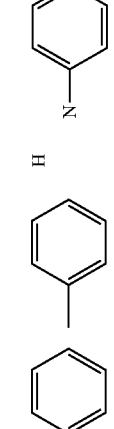 |  | 1 | 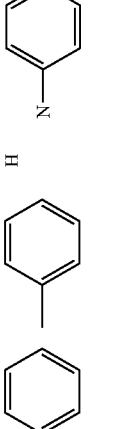 | H | H | 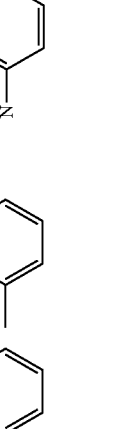 |
| 42 | 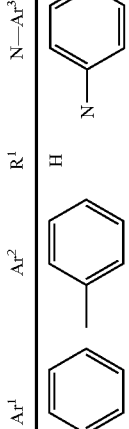 | 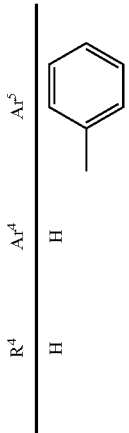 | H | 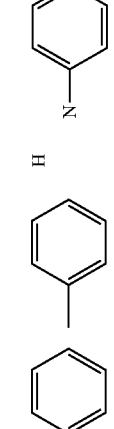 |  | 1 | 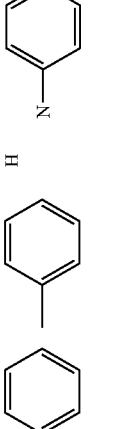 | H | H | 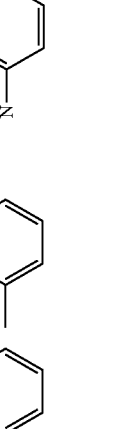 |
| 43 | 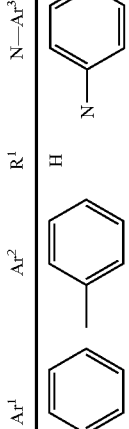 | 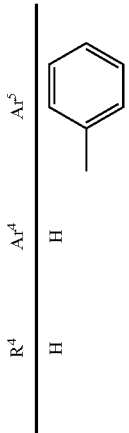 | H | 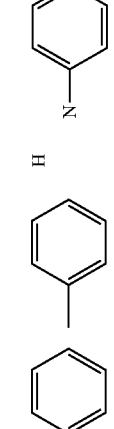 |  | 1 | 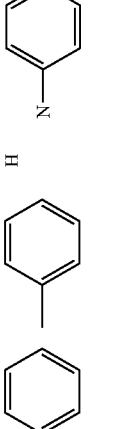 | H | H | 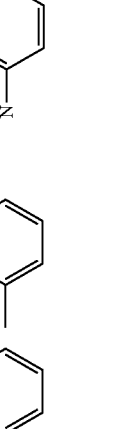 |
| 44 | 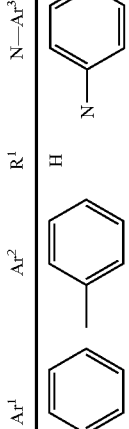 | 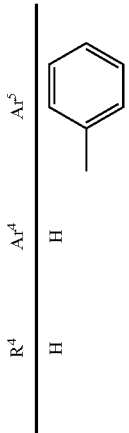 | H | 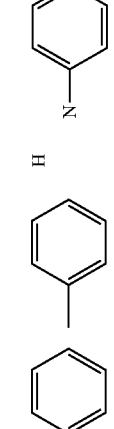 |  | 1 | 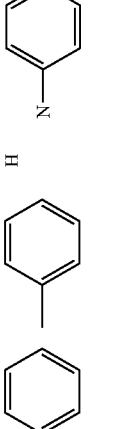 | H | H | 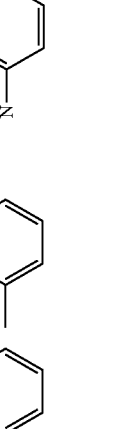 |
| 45 | 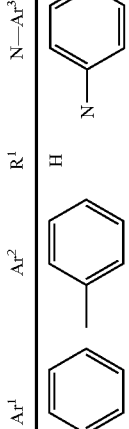 | 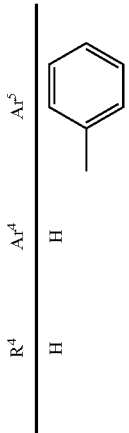 | H | 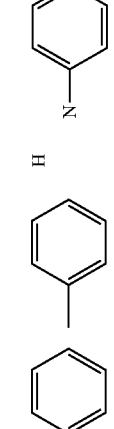 |  | 1 | 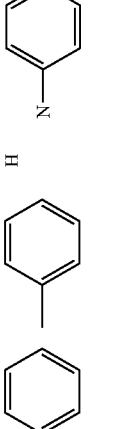 | 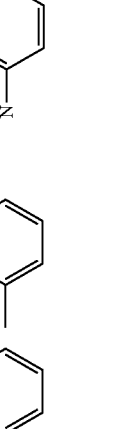 | H | 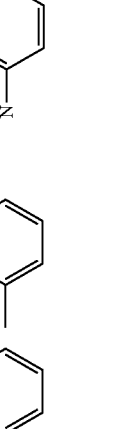 |

TABLE 10

| Example Compound No. | Ar¹ | Ar² | R¹ | N—Ar³ | N—Ar⁶ | n | CR²=CR³ | R⁴ | Ar⁴ | Ar⁵ |
|---|---|---|---|---|---|---|---|---|---|---|
| 46 | phenyl | phenyl | H | p-phenylene | 4-methyl-1-naphthyl | 2 | CH=CH—CH=CH | H | H | phenyl |
| 47 | phenyl | phenyl | H | p-phenylene | 4-methyl-1-naphthyl | 2 | CH=CH—CH=CH | H | H | 4-methoxyphenyl |
| 48 | phenyl | phenyl | H | p-phenylene | 4-methyl-1-naphthyl | 2 | CH=CH—CH=CH | H | —CH₃ | 4-methoxyphenyl |
| 49 | phenyl | phenyl | H | p-phenylene | 4-methyl-1-naphthyl | 2 | CH=CH—CH=CH | H | —CH₃ | 2-furyl |
| 50 | phenyl | phenyl | H | p-phenylene | 4-methyl-1-naphthyl | 2 | CH=CH—CH=CH | H | —CH₃ | 4-(2-phenylethenyl)phenyl |

TABLE 11
| No | Ar¹ | Ar² | R¹ | N—Ar³ | N—Ar⁶ | n | CR²=CR³ | R⁴ | Ar⁴ | Ar⁵ |
|---|---|---|---|---|---|---|---|---|---|---|
| 51 | 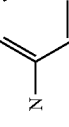 | 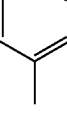 | H |  |  (4-methylnaphthyl) | 2 | CH=CH—CH=CH | H | —CH₃ | 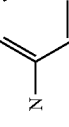 (p-tolyl) |
| 52 | 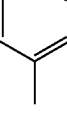 |  | H |  | 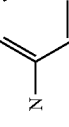 (4-methylnaphthyl) | 2 | 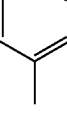 (4-OCH₃-phenyl) | H | H |  |
| 53 |  | 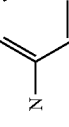 | H | 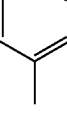 |  (4-methylnaphthyl) | 2 |  (4-N(CH₃)₂-phenyl) | H | H | 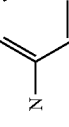 |
| 54 | | | H | | (4-methylnaphthyl) | 2 | (4-CH(CH₃)₂-phenyl) CH₃,H | H | H | |
| 55 | | | H | | 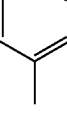 (4-Cl-phenyl) | 1 | CH=CH | H | H |  |

TABLE 12

| Example Compound No. | Ar¹ | Ar² | R¹ | N—Ar³ | N—Ar⁶ |
|---|---|---|---|---|---|
| 56 | phenyl | phenyl | H | N-(4-methylphenyl) | 3-methylphenyl |
| 57 | phenyl | phenyl | H | N-(4-methylphenyl) | 2-fluorophenyl |
| 58 | phenyl | phenyl | H | N-(4-methylphenyl) | 4-(CH₂CH₂F)phenyl |
| 59 | phenyl | phenyl | H | 3,5-dimethyl-4-methoxyphenyl | N-(4-methylphenyl) |
| 60 | phenyl | phenyl | H | 8-methyl-5,6,7,8-tetrahydronaphthalen-1-yl | N-(4-methylphenyl) |

| Example Compound No. | n | CR²=CR³ | R⁴ | Ar⁴ | Ar⁵ |
|---|---|---|---|---|---|
| 56 | 1 | CH=CH | H | H | phenyl |
| 57 | 1 | CH=CH | H | H | phenyl |
| 58 | 1 | CH=CH | H | H | phenyl |
| 59 | 1 | CH=CH | H | H | phenyl |
| 60 | 1 | CH=CH | H | H | phenyl |

TABLE 13

| Example Compound No. | Ar¹ | Ar² | R¹ | N—Ar³ | N—Ar⁶ | n | CR²=CR³ | R⁴ | Ar⁴ | Ar⁵ |
|---|---|---|---|---|---|---|---|---|---|---|
| 61 | 6-methylchroman | 6-methylchroman | H | 4-methylphenyl | 4-methylnaphthyl | 2 | CH=CH | H | H | phenyl |
| 62 | phenyl | phenyl | H | biphenyl | 4-methylphenyl | 1 | CH=CH | H | H | phenyl |
| 63 | phenyl | phenyl | H | 4-methylphenyl | 4-(phenylthio)phenyl | 1 | CH=CH | H | H | phenyl |
| 64 | phenyl | phenyl | H | 4-methylphenyl | 4-(4-methylphenoxy)phenyl | 1 | CH=CH | H | H | phenyl |
| 65 | phenyl | phenyl | H | 4-methylphenyl | 4-biphenyl | 1 | CH=CH | H | H | phenyl |

TABLE 14

| Example Compound No. | Ar¹ | Ar² | R¹ | N—Ar³ | N—Ar⁶ | n | CR²=CR³ | R⁴ | Ar⁴ | Ar⁵ |
|---|---|---|---|---|---|---|---|---|---|---|
| 66 | phenyl | phenyl | H | N-(4-methylphenyl) | 5-methyl-2-thienyl (N-linked) | 1 | CH=CH | H | H | phenyl |
| 67 | phenyl | phenyl | H | N-(4-methylphenyl) | 1,5-dimethyl-1H-pyrrol-2-yl (N-linked) | 1 | CH=CH | H | H | phenyl |
| 68 | phenyl | phenyl | H | N-(4-methylphenyl) | 1,5-dimethyl-1H-imidazol-2-yl (N-linked) | 1 | CH=CH | H | H | phenyl |
| 69 | phenyl | phenyl | H | N-(4-methylphenyl) | 5-methylbenzofuran-2-yl (N-linked) | 1 | CH=CH | H | H | phenyl |
| 70 | phenyl | phenyl | H | N-(4-methylphenyl) | 6-methylbenzoxazol-2-yl (N-linked) | 1 | CH=CH | H | H | phenyl |

TABLE 15
| Example Compound No. | Ar¹ | Ar² | R¹ | N—Ar³ | N—Ar⁶ | n | CR²=CR³ | R⁴ | Ar⁴ | Ar⁵ |
|---|---|---|---|---|---|---|---|---|---|---|
| 71 | 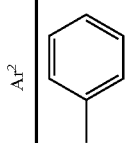 | 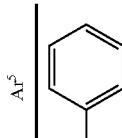 | H | 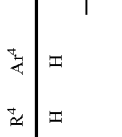 | 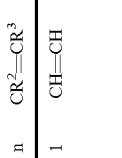 | 1 | CH=CH | H | H | 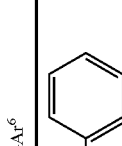 |
| 72 | 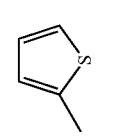 | 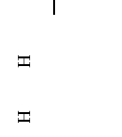 | H |  | 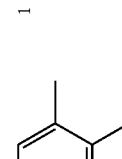 | 1 | CH=CH | H | H | 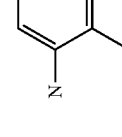 |
| 73 | 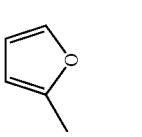 |  | H | 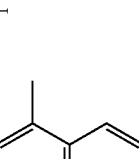 | 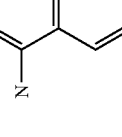 | 1 | CH=CH | H | H | 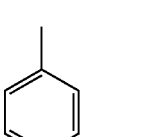 |
| 74 | 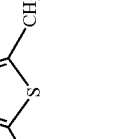 |  | H | 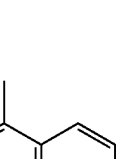 | 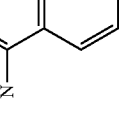 | 1 | CH=CH | H | H | 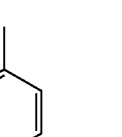 |
| 75 | 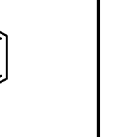 |  | H | 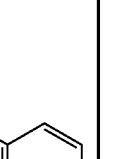 | 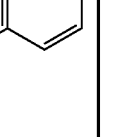 | 1 | CH=CH | H | H | 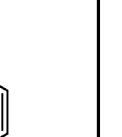 |

TABLE 16
| Example Compound No. | Ar¹ | Ar² | R¹ | N—Ar³ | N—Ar⁶ | n | CR²=CR³ | R⁴ | Ar⁴ | Ar⁵ |
|---|---|---|---|---|---|---|---|---|---|---|
| 76 | 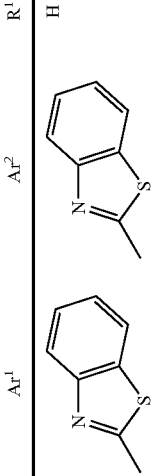 | 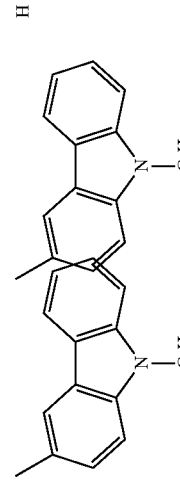 | H | 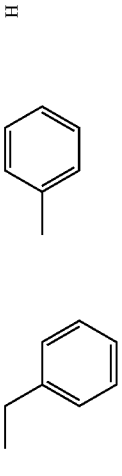 | 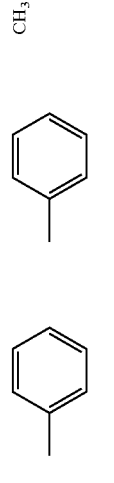 | 1 | CH=CH | H | H | 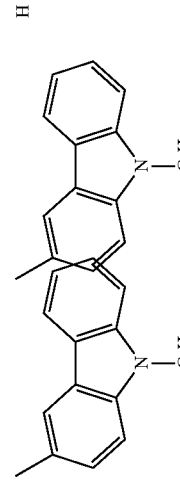 |
| 77 | 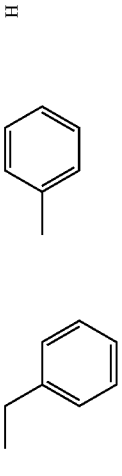 | 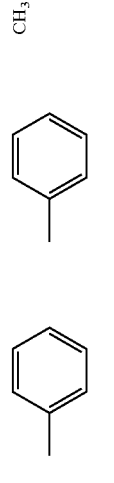 | H | 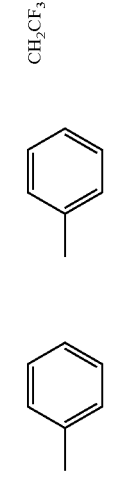 | 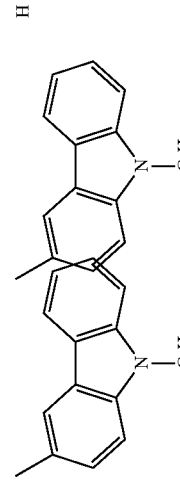 | 1 | CH=CH | H | H | 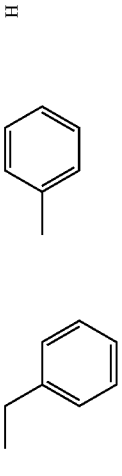 |
| 78 | 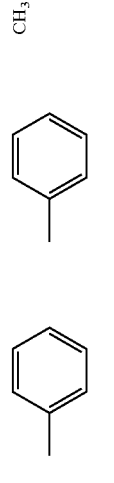 | 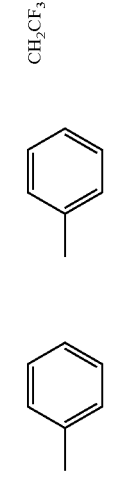 | H | 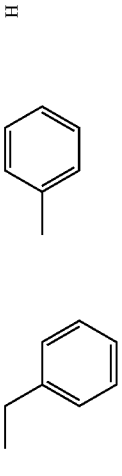 | 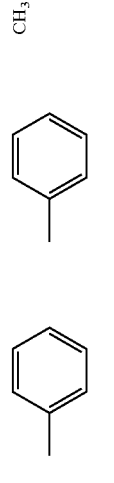 | 1 | CH=CH | H | H | 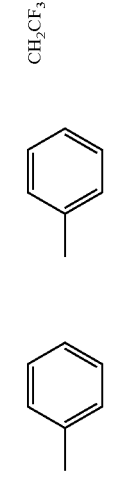 |
| 79 | 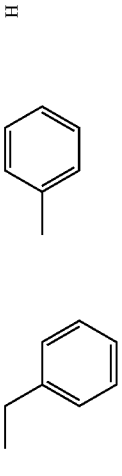 | 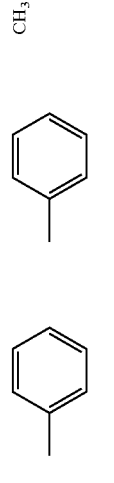 | CH₃ | 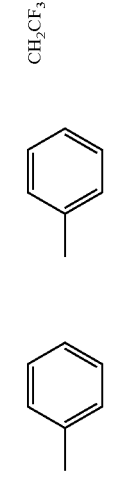 | | 1 | CH=CH | H | H | |
| 80 | | | CH₂CF₃ | | | 1 | CH=CH | H | H | |

In Tables 1 to 16, for $Ar^3$ and $Ar^6$, "N" is additionally shown in the cells in order to indicate the position to be connected to N.

The enamine compound represented by the above general formula (1) as the organic photoconductive material of the present invention can be produced in the following manner, for example.

To begin with, by a dehydration and condensation reaction between an aldehyde compound or ketone compound shown by the following general formula (3) and a secondary amine compound represented by the following general formula (4), an enamine intermediate shown by the following general formula (5) is produced.

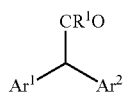
(3)

(In the formula $Ar^1$, $Ar^2$ and $R^1$ are the same as those defined in the above general formula (1)).

(4)

(In the formula $Ar^3$ and $Ar^6$ are the same as those defined in the above general formula (1)).

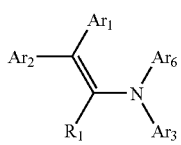
(5)

(In the formula $Ar^1$, $Ar^2$, $Ar^3$, $Ar^6$ and $R^1$ are the same as those defined in the above general formula (1)).

This dehydration and condensation reaction is carried out by the following manner, for example. An aldehyde compound or ketone compound represented by the general formula (3) and approximately the same molar amount of a secondary amine compound represented by the above general formula (4) are dissolved into an aromatic solvent or an alcohol or ether solvent, to prepare a solution. Specific examples of the usable solvent may include toluene, xylene, chlorobenzene and butanol, diethyleneglycol dimethylether. The prepared solution contains a catalyst such as p-toluene-sulfonic acid, camphor sulfonic acid, pyridinium-p-toluene-sulfonate or other acid catalysts. Further, it is heated to achieve reaction. The added amount of the catalyst is preferably one tenth (1/10) to one thousandth (1/1000), in molar equivalent, of the aldehyde or ketone compound represented by the above general formula (3), more preferably one twenty-fifth (1/25) to one five-hundredth (1/500), in molar equivalent, and optimally, one fiftieth (1/50) to one two-hundredth (1/200), in molar equivalent (to be referred to as "equivalent", hereinafter). Since water, which arises as a secondary product during reaction, inhibits the reaction, the generated water is removed out of the system as an azeotrope with the solvent. In this process, the enamine intermediate shown by the above general formula (5) can improve a high yield.

Next, the enamine intermediate represented by the above general formula (5) is bis-formylated by the Vilsmeier reaction or bis-acylated by the Friedel-Craft reaction to produce an enamine-bis-carbonyl intermediate shown by the following general formula (6). Upon production, when formation by the Vilsmeier reaction is performed, among enamine-bis-carbonyl intermediates shown by the following general formula (6) an enamine-aldehyde intermediate with $R^5$ being a hydrogen atom can be produced. When acylation by the Friedel-Craft reaction is performed, among enamine-calbonyl intermediates shown by the following general formula (6) an enamine-bis-ketone intermediate with $R^5$ being a group other than hydrogen atom can be produced.

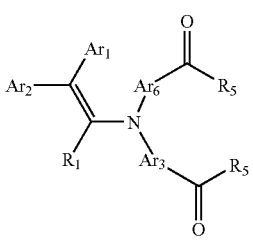
(6)

(In the formula $R^5$ indicates $R^4$ when n=0 and $R^2$ when n=1, 2 or 3 in the above general formula (1). $Ar^1$, $Ar^2$, $Ar^3$, $Ar^6$ and $R^1$ are the same as those defined in the above general formula (1)).

The Vilsmeier reaction is performed as follows, for example. Added to a solvent such as N,N-dimethylformamide (abbreviation: DMF), 1,2-dichloroethane or the like, are phosphorus oxychloride and N,N-dimethylformamide, phosphorus oxychloride and N-methyl-N-phenylformamide, or phosphorus oxychloride and N,N-diphenylformamide, so as to prepare a Vilsmeier reagent. Added to 2.0 to 2.3 equivalents of the prepared Vilsmeier reagent is 1.0 equivalent of the enamine intermediate represented by the general formula (5). The mixture is stirred for 2 to 8 hours while being heated at 60 to 110 deg. C. Then, this is hydrolyzed by an alkali solution such as a 1 to 8 N solution of sodium hydroxide, potassium hydroxide or the like. By this reaction, among the enamine-bis-carbonyl intermediates represented by the general formula (6), the enamine-aldehyde intermediate with $R^2$ being a hydrogen atom can improve at a high yield.

On the other hand, the Friedel-Craft reaction is performed as follows, for example. Added to a solvent such as 1,2-dichloroethane or the like, are 2.0 to 2.3 equivalents of a reagent prepared from aluminum chloride and oxychloride, and 1.0 equivalent of the enamine intermediate represented by the general formula (5). The mixture is stirred for 2 to 8 hours under a temperature of –40 to 80 deg. C. In this process, on a case by case basis it may be heated. Then, this is hydrolyzed by an alkali solution such as a 1 to 8N solution of sodium hydroxide, potassium hydroxide or the like. By this reaction, among the enamine-bis-carbonyl intermediates represented by the general formula (6), the enamine-bis-ketone intermediate with $R^2$ being a group other than a hydrogen atom can be produced at a high yield.

Finally, it is possible to produce an enamine compound represented by the above general formula (1), the organic photoconductive material of the present invention, by implementing the Wittig-Horner reaction wherein an enamine-biscarbonyl intermediate represented by the general formula (6) is reacted with a Wittig reagent represented by the following general formula (7) under a basic condition.

In this reaction, when the Wittig reagent represented by the following general formula (7-1) is used, among the enamine compounds represented by the above general formula (1), those with n being 0 can be obtained. When the Wittig reagent represented by the following general formula (7-2) is used, among the enamine compounds represented by the above general formula (1), those with n being 1, 2 or 3 can be obtained.

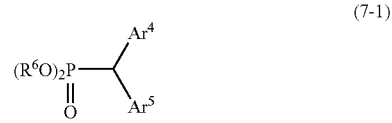
(7-1)

(In the formula $R^6$ indicates an alkyl group optionally containing a substituent or an aryl group optionally containing a substituent. $Ar^4$ and $Ar^5$ are the same as those defined in the above general formula (1)).

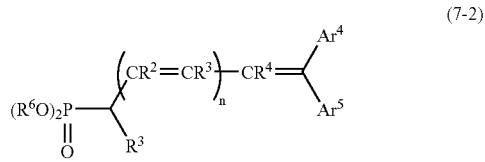
(7-2)

(In the formula $R^6$ indicates an alkyl group optionally containing a substituent or an aryl group optionally containing a substituent. "n" denotes an integer of 1 to 3. $Ar^4$, $Ar^5$, $R^2$, $R^3$ and $R^4$ are the same as those defined in the above general formula (1)).

This Wittig-Horner reaction is performed as follows, for example. Added to a solvent such as toluene, xylene, diethylether, tetrahydrofran (abbreviation: THF), ethyleneglycol dimethylether, N,N-dimethylformamide, dimethylsulphoxyde or the like, are 1.0 equivalent of the enamine-carbonyl intermediate represented by the general formula (6), 2.0 to 2.30 equivalents of a Wittig reagent represented by the general formula (7-1) or (7-2) and 2.0 to 2.5 equivalents of a metal alkoxide base such as potassium t-butoxide, sodium ethoxide, sodium methoxide or the like. The mixture is stirred for 2 to 8 hours under room temperature or while being heated at a temperature of 30 to 60 deg. C. By this reaction, the enamine compound represented by the above general formula (1) can be produced at a high yield.

The electrophotographic photoreceptor (to be also referred to simply as "photoreceptor" hereinafter) according to the present invention uses the above-described organic photoconductive material of the present invention represented by the above general formula (1), or by (2), for example, and can be embodied by various modes. This will be detailed hereinafter with reference to the drawings.

FIG. 1 is a simplified schematic sectional view showing an electrophotographic photoreceptor 1 as one example of the electrophotographic photoreceptor of the present invention. Electrophotographic photoreceptor 1 is a lamination type photoreceptor. The lamination type photoreceptor consists of a sheet-like conductive substrate 11 formed of a conductive material and a photosensitive layer 14 having a laminated structure. The photosensitive layer 14 is formed on the support in which a charge generation layer 15 containing a charge generation material 12 and a charge transport layer 16 including a charge transport material 13 and a binder resin 17 for binding charge transport material 13 are provided in layers in this order from conductive substrate 11 toward the outside (in the drawing, charge generation material 12 and charge transport material 13 are depicted with emphasis but these materials are uniformly dispersed in respective layers or with the components such as binder resin etc.).

Charge transport layer 16 contains as charge transport material 13 the enamine compound having a high charge mobility, as the organic photoconductive material of the present invention, represented by the above general formula (1) or by (2), for example. Accordingly, it is possible to obtain an electrophotographic photoreceptor, which presents a high electrified potential, high sensitivity and high enough light response as well as excellent durability and will not degrade in these characteristics under a low-temperature environment or in a high-speed process. Since it is possible to realize a high charge transport capability without having photosensitive layer 14 contain polysilane or the like, it is possible to obtain a reliable electrophotographic photoreceptor free from characteristics degradation due to exposure to light. Further, as stated already, photosensitive layer 14 has a laminated structure of charge generation layer 15 containing charge generation material 12 and charge transport layer 16 containing charge transport material 13. Since the function of charge generation and the function of charge transport are assigned to different layers in the above way, it is possible to select optimal materials for the function of charge generation and the function of charge transport, respectively. As a result, it is possible to obtain an electrophotographic photoreceptor presenting a higher sensitivity and increased stability and high durability against repeated usage.

As the conductive material constituting conductive substrate 11, metals such as, for example aluminum, aluminum alloy, copper, zinc, stainless steel, titanium and the like can be used. The material should not be limited to these metallic materials. It is also possible to use a substrate of a polymer such as polyethylene terephthalate, nylon, polystyrene etc., or a hard paper or glass substrate, with its surface laminated with metal foil, deposited with a metallic material, deposited or applied with a conductive compound layer of a conductive polymer, tin oxide, indium oxide or the like. Though conductive substrate 11 is given in a sheet-like form when it is used for electrophotographic photoreceptor 1, the configuration is not limited to this and may be given in a tubular, cylindrical, endless belt or other form.

So far as the image quality is not affected, the surface of conductive substrate 11 may be optionally subjected to anodic oxide coating treatment, surface treatment with chemicals, hot water, etc., coloring treatment, or diffuse reflection treatment by roughening the surface, etc. In the case of an electrophotographic process using laser as an exposure light source, since the wavelengths of the laser light are in phase, the incident laser light may cause interference with the light reflected by the interior of the electrophotographic photoreceptor, and the interference fringe due to the interference of light may appear on the image, causing image defects. It is possible to prevent such image defects due to interference of laser light of in-phase wavelengths, by treating the surface of conductive substrate 11 in the aforementioned manner.

Charge generation layer 15 contains as its main component, charge generation material 12 that generates electricity as it absorbs light. Examples of effective materials as charge generation material 12 include: azo pigments such as monoazo pigments, bisazo pigments trisazo pigments and the like; indigo pigments such as indigo, thioindigo and the like; perylene pigments such as peryleneimide, perylene acid anhydride and the like; polycyclic quinone pigments such as anthraquinone and pyrenequinone and the like; phthalocyanine pigments such as metal phthalocyanine, metal-free phthalocyanine and the like; squarylium dyes; pyrylium salts and thiopyrylium salts; triphenylmethane dyes and; inorganic materials such as selenium, amorphous silicon and the like. These charge generation materials may be used alone or in combination of two or more kinds.

Of these charge generation materials, oxotitanium phthalocyanine may be preferably used. Since oxotitanium phthalocyanine is a charge generation material having high charge generation efficiency and charge injection efficiency, it can generate a great amount of charge by absorbing light and efficiently inject the generated charge into charge transport material 13 without accumulating it therein. Further, as stated above charge transport material 13 employs an organic photoconductive material having a high charge mobility, represented by the above general formula (1) or by (2), for example. Accordingly, the charge generated in charge generation material 12 by light absorption is efficiently injected and smoothly transported into charge transport material 13, so that it is possible to obtain an electrophotographic photoreceptor that can present a high sensitivity and a high resolution.

Charge generation material 12 may be used in combination with sensitization dyes such as triphenylmethane dyes typified by methylviolet, crystal violet, night blue, Victoria blue, etc.; acridine dyes typified by erythrosine, rhodamine B, rhodamine 3R, acridine orange, flaveosine, etc.; thiazine dyes typified by methylene blue, methylene green, etc.; oxazine dyes typified by Capri blue, meldra blue, etc., cyanine dyes, styryl dyes, pyrylium salt dyes, thiopyrylium salt dyes and the like.

Formation of charge generation layer 15 can be done by a vacuum deposition method of depositing charge generation material 12 over conductive substrate 11, by a method of dispersing charge generation material 12 in a solvent and applying the resultant coating liquid for charge generation layer over conductive substrate 11, etc. Of these, a preferable method is achieved by dispersing charge generation material 12, in a publicly known conventional manner, into a binder resin solution which is obtained by mixing a binder resin as a binding agent into a solvent, and applying the resultant application liquid over conductive substrate 11. This method will be described next.

As the binder resin, use is made of one kind of resin or mixture of two or more resins, selected from the group including: resins such as polyester resin, polystyrene resin, polyurethane resin, phenol resin, alkyd resin, melamine resin, epoxy resin, silicone resin, acrylic resin, methacrylic resin, polycarbonate resin, polyacrylate resin, phenoxy resin, polyvinyl butyral resin, polyvinyl formal resin, etc.; and copolymer resins containing two or more kinds of repetition units constituting these resins. As specific examples of copolymer resin, insulating resins such as vinylchloride-vinylacetate copolymer resin, vinylchloride-vinylacetate-maleic anhydride copolymer resin, acrylonitrile-styrene copolymer resin, etc. may be considered. The binder resin is not limited to these, and it is possible use general-purpose resins as a binder resin.

As the solvent, halide hydrocarbons such as dichloromethane, dichloroethane, etc., ketones such as acetone, methylethyl ketone, cyclohexanone, etc., esters such as ethylacetate, butylacetate, etc., ethers such as tetrahydrofran (THF), dioxane, etc., alkylethers of ethylene glycol such as 1,2-dimethoxyethane etc., aromatic hydrocarbons such as benzene, toluene, xylene etc., aprotic solvents such as N,N-dimethylformamide, N,N-dimethylacetoamide, etc., can be used. A mixture solvent of two or more of these solvents can also be used.

As to the blending ratio of charge generation material 12 and the binder resin, the proportion of charge generation material 12 preferably ranges from 10 mass % to 99 mass %. When the proportion of charge generation material 12 is lower than 10 mass %, the sensitivity degrades. When the proportion of charge generation material 12 exceeds 99 mass %, not only the film strength of charge generation layer 15 lowers but also the dispersibility of charge generation material 12 lowers. This will increase coarse particles in number, hence the surface charge in areas other than that to be erased by exposure to light will decrease. As a result, image defects, particularly, image fogging or minute black spots being formed by adherence of toner to the white background, will tend to occur more frequently. This is why the proportion is specified to range from 10 mass % to 99 mass %.

Before dispersing charge generation material 12 into a binder resin solution, the charge generation material 12 may be crushed beforehand by a crusher. As the crusher for the crushing process, ball mills, sand mills, atriters, vibration mills, ultrasonic dispersers, etc. may be used.

As a disperser for dispersing charge generation material 12 into a binder resin solution, a paint shaker, ball mill, sand mill or the like, can be used. Forth is dispersing process appropriate conditions should be selected so that no impurity contamination will occur due to abrasion of the container in use and parts of the disperser.

For applying the charge generation layer coating liquid that is obtained by dispersing charge generation material 12 in a binder resin solution, spraying, bar coating, roll coating, blade technique, ring technique, dip coating and the like can be used. Of these coating techniques, an optimal method can be selected taking into account the physical properties of application, productivity and other factors. Particularly, dip coating is a technique to form a coating layer on conductive substrate 11 by immersing conductive substrate 11 into a coating tank filled with a coating liquid and then drawing it up with a uniform speed or successively varying speeds. Since this technique is relatively simple and high in productivity and cost-efficient, it is widely used for production of electrophotographic photoreceptors. In this connection, in order to stabilize the dispersibility of the coating liquid the machine for dip coating technique may be equipped with a coating liquid disperser, typified by an ultrasonic generator.

The film thickness of charge generation layer 15 is preferably not smaller than 0.05 µm and not greater than 5 µm, more preferably, not smaller than 0.1 µm and not greater than 1 µm. When charge generation layer 15 is smaller in film thickness than 0.05 µm, the light absorption efficiency lowers, hence the sensitivity degrades. When the film thickness of charge generation layer 15 exceeds 5 µm, movement of charge inside the charge generation layer imposes a rate-limiting step on the process of erasing charge on the photoreceptor surface, hence the sensitivity degrades. This is why the film thickness is specified to range from 0.05 µm to 5 µm.

Charge transport layer 16 is obtained by having the organic photoconductive material of the present invention, represented by the above general formula (1) or by (2), for example, contained as charge transport material 13 capable of accepting and transporting the charge generated in charge generation material 12, into binder resin 17. Use of the organic photoconductive material represented by the above general formula (1) or by (2), for example, is made by selecting one compound alone or by mixing two or more kinds in combination, from the group including example compounds shown in Tables 1 to 16 above.

The organic photoconductive material represented by the above general formula (1) or by (2), for example, may be used by mixing itself with other charge transport materials.

Examples of the other charge transport materials may include carbazole derivatives, oxazole derivatives, oxadiazole derivatives, thiazole derivatives, thiadiazole derivatives, triazole derivatives, imidazole derivatives, imidazolone derivatives, imidazolidine derivatives, bis-imidazolidine derivatives, styryl compounds, hydrazone compounds, polycyclic aromatic compounds, indole derivatives, pyrazoline derivatives, oxazolone derivatives, benzimidazole derivatives, quinazoline derivatives, benzofuran derivatives, acridine derivatives, phenazine derivatives, aminostilbene derivatives, triarylamine derivatives, triarylmethane derivatives, phenylenediamine derivatives, stilbene derivatives, benzidine derivatives. Polymers having groups derived from these compounds in the principal chain or as side chains, for example poly-N-vinycarbazole, poly-1-vinylpyrene, poly-9-vinylanthracene, etc., may also be used.

However, in order to realize particularly high charge transport capability, it is preferable that the whole of charge transport material 13 is constituted of the organic photoconductive material of the present invention, represented by the above general formula (1), by (2), for example.

For binder 17 used for charge transport layer 16, one compatible with charge transport material 13 may be selected. Specific examples may include vinyl polymer resins such as polymethyl methacrylate resin, polystyrene resin, polyvinyl chloride resin etc., and copolymer resins of these, and polycarbonate resin, polyester resin, polyester-carbonate resin, polysulfone resin, phenoxy resin, epoxy resin, silicone resin, polyarylate resin, polyamide resin, polyether resin, polyurethane resin, polyacrylamide resin, phenol resin and the like. Thermosetting resins of the above resins being partially cross-linked may also be used. These resins may be used alone or in combination of two or more kinds. Among the aforementioned resins, polystyrene, polycarbonate resin, polyacrylate resin and polyphenylene oxide are excellent in electric insulation with a volume resistivity of $10^{13}\Omega$ or greater, and also excellent in film formability and potential characteristics, etc. Accordingly, these are particularly preferable to be used for binder resin 17.

In general, the ratio A/B of charge transport material 13 (A) and binder resin 17 (B) is about 10/12 in mass ratio, but in the electrophotographic photoreceptor 1 of the present invention, it is specified to be 10/12 to 10/30 in mass ratio.

As described above, since charge transport material 13 contains the organic photoconductive material of the present invention, which is represented by the above general formula (1) or by (2), for example, and has a high charge mobility, it is possible to maintain the light response even if the binder is added at a ratio, specifically, the aforementioned ratio A/B is set at 10/12 to 10/30, which is higher than that for the conventionally known charge transport material. Accordingly, it is possible to improve the abrasion resistance of charge transport layer 16 and improve the durability of the electrophotographic photoreceptor without degradation of light response.

If the ratio of binder resin 17 is so high that the aforementioned ratio A/B is lower than 10/30, the coating liquid when charge transport layer 16 is formed by dip coating increases in viscosity, and this causes lowering of the coating speed, resulting in markedly low productivity. If the solvent quantity in the coating liquid is increased in order to inhibit increase in the viscosity of the coating liquid, brushing may occur and cause whitening in the formed charge transport layer 16. On the other hand, if the ratio of binder resin 17 is so low that the aforementioned ratio A/B exceeds 10/12, the abrasion resistance becomes low compared to that when the ratio of binder 17 is high, hence this results in increase in the amount of abrasion of the photosensitive layer. This is why the ratio is specified to be equal to 10/12 or higher and equal to 10/30 or lower.

In order to improve film formability, flexibility and surface smoothness, charge transport layer 16 may be added, as required, with additives such as plasticizers, leveling agents and the like. Examples of plasticizers may include dibasic acid esters, fatty acid esters, phosphoric acid esters, phthalic acid esters, chlorinated paraffins, epoxy plasticizers and the like. Examples of leveling agents may include silicone leveling agents etc.

In order to enhance mechanical strength and electric characteristics of charge transport layer 16, inorganic or organic fine particles may be added.

Further, charge transport layer 16 may be added, as required, with various kinds of additives such as an oxidation inhibitor, sensitizer, etc. These additives make it possible to improve potential characteristics and stability as a coating liquid and also reduce fatigue deterioration when the photoreceptor has been repeatedly used to improve durability.

As an example of oxidation inhibitor, hindered phenol derivatives and hindered amine derivatives are preferably used. The hindered phenol derivative is preferably used in the proportion ranging from 0.1 mass % to 50 mass % relative to charge transport material 13. The hindered amine derivative is preferably used in the proportion ranging from 0.1 mass % to 50 mass % relative to charge transport material 13. The hindered phenol derivative and hindered amine derivative may be used by mixture. In this case, the total usage amount of the hindered phenol derivative and hindered amine derivative preferably ranges from 0.1 mass % to 50 mass % relative to charge transport material 13. When the usage amount of the hindered phenol derivative, the usage amount of the hindered amine derivative or the total amount of the hindered phenol derivative and hindered amine derivative is lower than 0.1 mass %, it is impossible to have high enough effect of improvement in the stability of the coating liquid and improvement in the durability of the photoreceptor. When it exceeds 50 mass %, the photoreceptor characteristics will be adversely affected. Accordingly, these usage amount is specified to be from 0.1 mass % to 50 mass %.

Charge transport layer 16 is formed, in a similar manner as, for example the aforementioned charge generation layer 15 is formed, by dissolving or dispersing charge transport material 13 and binder resin 17, and the aforementioned additives, if required, into an appropriate solvent to prepare a charge transport layer coating liquid, then applying the coating liquid over charge generation layer 15 by spraying, bar coating, roll coating, blade technique, ring technique, dip coating or the like. Of these coating techniques, dip coating is also most utilized to form charge transport layer 16 because of its being excellent in various respects as mentioned above.

For the solvent used for the coating liquid, one solvent alone, or two or more solvents by mixture, selected from the group of aromatic hydrocarbons such as benzene, toluene, xylene, monochlorobenzene, etc., halide hydrocarbons such as dichloromethane, dichloroethane, etc., ethers such as tetrahydrofran (THF), dioxane, dimethoxymethyl ether, etc., aprotic solvents such as N,N-dimethylformamide, etc., can be used. Further, the aforementioned solvent can be used by adding extra solvents such as alcohols, acetonitrile or methylethyl ketone, etc.

The film thickness of charge transport layer 16 is preferably not smaller than 5 μm and not greater than 50 μm, and more preferably not smaller than 10 μm and not greater than 40 μm. If the film thickens of charge transport layer 16 is smaller than 5 μm, the charge retaining function of the photoreceptor surface lowers. If the film thickness of charge transport layer 16 exceeds 50 μm, the photoreceptor resolution lowers. This is why the thickness is specified to be not smaller than 5 μm and not greater than 50 μm.

Further, in order to enhance sensitivity and inhibit increase in residual potential and fatigue as a result of repeated usage, one or more kinds of electron acceptor substances and dyes may be added.

As the electron acceptor substance, electron absorbing materials including anhydrides such as succinic anhydride, maleic anhydride, phthalic anhydride, 4-chlor naphthalic anhydride, etc., cyano compounds such as tetracyanoethylene, terephthal malonic dinitrile, etc., aldehydes such as 4-nitrobenzaldehyde, etc., anthraquinones such as anthraquinone, 1-nitro anthraquinone, etc., polycyclic and heterocyclic nitro compounds such as 2,4,7-trinitrofluorenone, 2,4,5,7-tetranitrofluorenone, etc., and diphenoquinone compounds as well as polymerized materials of these electron absorbing materials can be used.

Examples of the dyes that can be used, include organic photoconductive compounds such as xanthene dyes, thiazine dyes, triphenylmethane dyes, quinoline pigments, copper phthalocyanine, etc. These organic photoconductive compounds function as an optical sensitizer.

The surface of photosensitive layer 14 may be covered with a protective layer. Provision of a protective layer provides an improved abrasion resistance for photosensitive layer 14 and can prevent photosensitive layer 14 from receiving adverse chemical influence from ozone, nitrogen oxides generated by corona discharge upon charging the photoreceptor surface. The protective layer may be formed by that of a resin such as a resin containing an inorganic filler, that of an inorganic oxide, etc.

Figure 2:
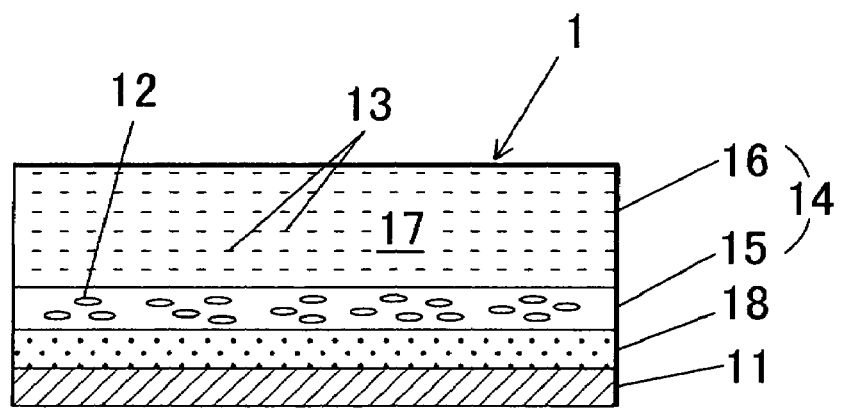
FIG. 2 is a simplified schematic sectional view showing an electrophotographic photoreceptor as another example of the present embodiment mode.

FIG. 2 is a simplified schematic sectional view showing the configuration of an electrophotographic photoreceptor 2 as another embodiment mode of an electrophotographic photoreceptor of the present invention. Electrophotographic photoreceptor 2 is similar to electrophotographic photoreceptor 1 shown in FIG. 1, so that the corresponding components are allotted with the same reference numerals and description is omitted. The noticeable point is that an intermediate layer 18 is provided between conductive substrate 11 and photosensitive layer 14.

When no intermediate layer 18 is present between conductive substrate 11 and photosensitive layer 14, electric charge is injected from conductive substrate 11 into photosensitive layer 14 so that the electrification capability of photosensitive layer 14 lowers and the surface charge in areas other than that in the areas to be erased by exposure to light decreases, possibly causing image fogging and other defects. Particularly, when a reversal development process is used for image forming, areas with the surface charge reduced by exposure to light are developed with images of toner. Accordingly, if the surface charge is reduced due to the factors other than exposure to light, toner adheres to the white background, producing image fogging or causing black spot defects from minute black dust. This leads to marked degradation of image quality.

Specifically, the electrification capability degrades at a micro level due to a certain defect of conductive substrate 11 or photosensitive layer 14, producing image fogging with black spots, hence causing serious image defects. Since provision of an intermediate layer 18 as stated above makes it possible to prevent electric charge from entering photosensitive layer 14 from conductive substrate 11, it is possible to prevent lowering of the electrification capability of photosensitive layer 14, hence inhibit reduction of the surface charge in the areas other than that to be erased by exposure to light, and prevent defects such as image fogging etc. from occurring.

Also, since provision of intermediate layer 18 makes it possible to make the conductive substrate 11 surface uniform by covering the defects on that surface, it is possible to enhance the film formability of photosensitive layer 14. It is also possible to prevent photosensitive layer 14 from peeling from conductive substrate 11 and enhance the adhesiveness between conductive substrate 11 and photosensitive layer 14.

For intermediate layer 18, a resin layer of various resin materials, an anodized-aluminum layer, or the like can be used. As the resin materials forming the resin layer, resins such as polyethylene resin, polypropylene resin, polystyrene resin, acrylic resin, vinyl chloride resin, vinyl acetate resin, polyurethane resin, epoxy resin, polyester resin, melamine resin, silicone resin, polyvinylbutyral resin and polyamide resin, etc.; copolymer resins containing two or more kinds of repetition units constituting these resins; and casein, gelatin, polyvinyl alcohol, ethyl cellulose, and the like can be considered. Of these, polyamide resin is preferably used, and use of alcohol-soluble nylon resins is particularly preferable. Preferable examples of alcohol-soluble nylon resins may include: so-called copolymer nylons which are copolymers of 6-nylon, 6,6-nylon, 6,10-nylon, 11-nylon, 2-nylon and/or the like; and chemically modified nylon resins such as N-alkoxymethyl modified nylon and N-alkoxyethyl modified nylon.

Intermediate layer 18 may contain particles of metal oxides and the like. Content of these particles enables adjustment of the volume resistivity of intermediate layer 18 and enhances prevention against injection of electric charge from conductive substrate 11 into photosensitive layer 14 as well as maintenance of the electric characteristics of the photoreceptor under various environments.

Examples of the metal oxide particles may include particles of titanium oxide, aluminum oxide, aluminum hydroxide, tin oxides and the like.

When particles of metal oxides and the like are included in intermediate layer 18, intermediate layer 18 may be formed, for example, by dispersing these particles into a resin solution with the aforementioned resin dissolved therein to prepare an intermediate layer coating liquid, and applying the coating liquid over conductive substrate 11.

The solvent of the resin solution may use water or various organic solvents. Particularly, preferable use is made of single solvents such as water, methanol, ethanol, butanol and the like, or mixed solvents such as mixtures of water and an alcohol, mixtures of two or more alcohols, mixtures of acetone, dioxolane or the like and an alcohol, mixtures of a chlorine solvent such as dichloroethane, chloroform, trichloroethane and the like and an alcohol.

Dispersing the aforementioned particles into the resin solution may be done by a typical method using a ball mill, sand mill, attriter, vibration mill, ultrasonic disperser or the like.

As to the total content C of the resin and metal oxide in the intermediate layer coating liquid relative the content D of the solvent used for the intermediate layer coating liquid, C/D in mass ratio, is preferably 1/99 to 40/60, more preferably 2/98 to 30/70. The ratio between the resin and the metal oxide (resin/metal oxide) is preferably, 90/10 to 1/99 and more preferably, 70/30 to 5/95, in terms of mass ratio.

For applying the intermediate layer coating liquid, spraying, bar coating, roll coating, blade technique, ring technique, dip coating and the like can be used. Particularly, since dip coating is relatively simple and excellent in productivity and cost as already mentioned, this technique is mainly used to form intermediate layer 18.

The film thickness of intermediate layer 18 is preferably not smaller than 0.01 μm and not greater than 20 μm, more preferably, not smaller than 0.05 μm and not greater than 10 μm. When intermediate layer 18 is smaller in film thickness than 0.01 μm, it does not provide the inherent function of intermediate layer 18. That is, it cannot cover the defects of conductive substrate 11, unable to provide uniform surface and prevent charge injection from conductive substrate 11 into photosensitive layer 14, resulting in lowering of the electrification capability of photosensitive layer 14. Specifying the film thickness of intermediate layer 18 to be greater than 20 μm, not only makes it difficult to form intermediate layer 18 when the intermediate layer 18 is formed by dip coating but also makes it impossible to form photosensitive layer 14 uniformly over intermediate layer 18, hence the sensitivity of the photoreceptor lowers, resulting in being unpreferable.

Figure 3:
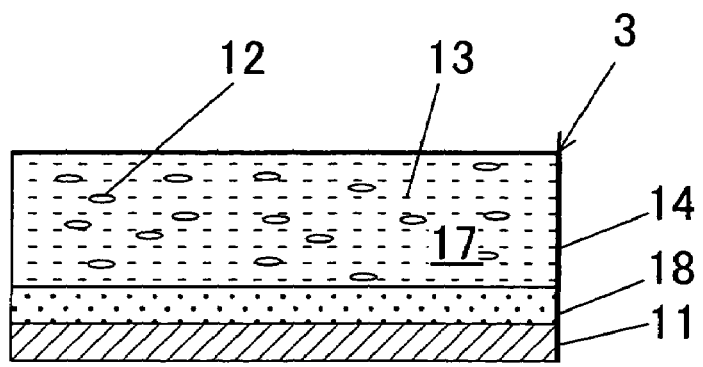
FIG. 3 is a simplified schematic sectional view showing an electrophotographic photoreceptor as still another example of the present embodiment mode.

FIG. 3 is a simplified schematic sectional view showing an electrophotographic photoreceptor 3 as still another embodiment mode of the present invention. Electrophotographic photoreceptor 3 is similar to electrophotographic photoreceptor 2 shown in FIG. 2, so that the corresponding components are allotted with the same reference numerals and description is omitted.

The noticeable point is that electrophotographic photoreceptor 3 is a single layered photoreceptor having a photosensitive layer 14 of a single layered structure in which both charge generation material 12 and charge transport material 13 are contained in a binder resin 17.

Photosensitive layer 14 is formed in the same method as that for forming the aforementioned charge transport layer 13. For example, the aforementioned charge generation material 12, the charge transport material 13 including the organic photoconductive material of the present invention, represented by the above general formula (1) or specifically by (2), and binder resin 17 are dissolved or dispersed into an appropriate solvent already mentioned, to prepare a photosensitive layer coating liquid. This photosensitive layer coating liquid is applied over intermediate layer 18 by dip coating or the like to form the photosensitive layer.

The ratio of charge transport material 13 and binder resin 17 in photosensitive layer 14 is 10/12 to 10/30 in mass ratio, like the ratio A/B of charge transport material 13 and binder resin 17 in the aforementioned charge transport layer 16.

The film thickness of photosensitive layer 14 is preferably not smaller than 5 μm and not greater than 100 μm, and more preferably not smaller than 10 μm and not greater than 50 μm. If the film thickness of photosensitive layer 140 is smaller than 5 μm, the charge retaining capability of the photoreceptor surface lowers. If the film thickness of photosensitive layer 140 exceeds 100 μm, the productivity lowers. This is why the thickness is specified to be not smaller than 5 μm and not greater than 100 μm.

The electrophotographic photoreceptor according to the present invention should not be limited to the above-described configurations shown in FIGS. 1 to 3, but various kinds of layered structures can be adopted.

Each layer of the photoreceptor may be added, if required, with various additives such as antioxidants, sensitizers, UV absorbers, etc. This makes it possible to improve potential characteristics. This also enhances stability of the coating liquid in forming the layers by application. Further, it is also possible to reduce the fatigue deterioration due to repeated use of the photoreceptor and improve durability.

As an antioxidant, phenol compounds, hydroquinone compounds, tocopherol compounds, amine compounds, etc., can be considered. The antioxidant is preferably added in an amount ranging from 0.1 mass % to 50 mass % relative to charge transport material 13. If the usage amount of the antioxidant is lower than 0.1 mass %, it is impossible to obtain high enough effect of improvement in the stability of the coating liquid and improvement in the durability of the photoreceptor. When the usage amount of the antioxidant exceeds 50 mass %, the photoreceptor characteristics are adversely affected. This is why the proportion is specified to range from 0.1 mass % to 50 mass %.

Next, an image forming apparatus having an electrophotographic photoreceptor of the present invention will be described. However, the image forming apparatus according to the present invention should not be limited to the following description.

Figure 4:
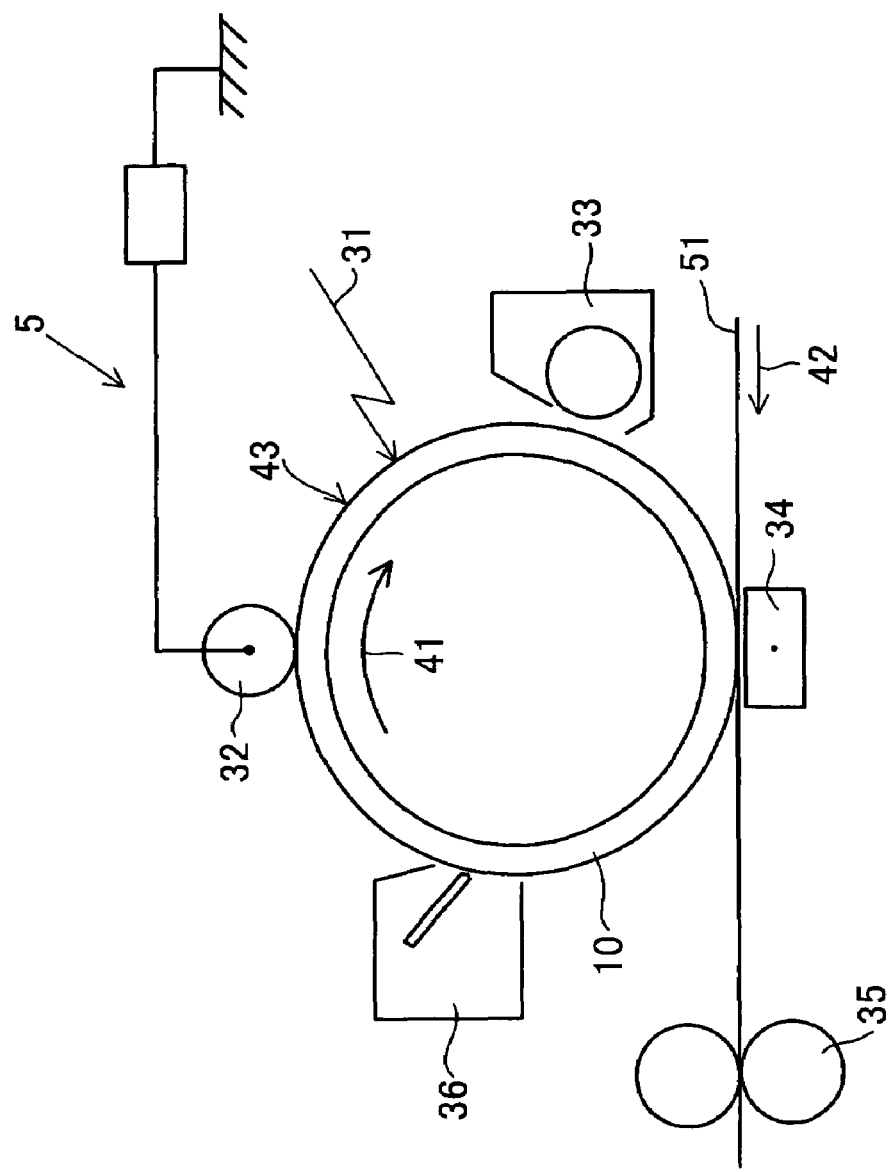
FIG. 4 is a simplified structural diagram showing an image forming apparatus configuration having an electrophotographic photoreceptor according to the present invention.

FIG. 4 is a simplified structural diagram showing an image forming apparatus configuration having an electrophotographic photoreceptor according to the present invention.

As shown in the figure, an image forming apparatus 5 has an electrophotographic photoreceptor 10 (to be referred to merely as "photoreceptor 10") of the present invention. Photoreceptor 10 has a cylindrical structure and is rotationally driven by an driving means at a predetermined peripheral speed in the direction designated at a reference numeral 41. Arranged around photoreceptor 10 along the rotational direction of photoreceptor 10 are a charger 32, an semiconductor laser, a developing device 33, a transfer charger 34 and a cleaner 36, in the order mentioned. A fixing unit 35 is provided in the traveling direction of print paper 51.

The image forming process by this image forming apparatus 5 will be described. First, photoreceptor 10 is uniformly charged by contact type or non-contact type charger 32 so that the surface 43 that faces charger 32 is electrified at a predetermined positive or negative potential. Then a laser beam 31 is emitted from a semiconductor laser, so that the surface 43 of photoreceptor 10 is exposed to light. Laser beam 31 repeatedly scans in the main scan direction or in the longitudinal direction of photoreceptor 10. As a result, an electrostatic latent image is formed sequentially on surface 43 of photoreceptor 10. The electrostatic latent image is developed into a toner image by developing device 33 which is located on the downstream side, with respect to the direction of rotation, of the focalized point of laser beam 31.

In synchronism with exposure of photoreceptor 10, print paper 51 is fed in the direction designated at a reference numeral 42 into transfer charger 34 located on the downstream side of developing device 33 with respect to the direction of rotation.

The toner image formed on surface 43 of photoreceptor 10 by developing device 33 is transferred to the print paper 51 surface by transfer charger 34. The print paper 51 with a toner image transferred thereon is conveyed by a conveying belt to fixing unit 35, whereby the toner image is fixed to print paper 51 to form a copy of an image.

The toner remaining on surface 43 of photoreceptor 10 is removed by cleaner 36 which is provided together with a erasing lamp and located further downstream of transfer charger 34 and upstream of charger 32 with respect to the direction of rotation. Photoreceptor 10 is rotated again to repeat the above process to form images on print paper 51. The print paper 51 thus formed with an image is discharged to the outside of image forming apparatus 5.

Since the electrophotographic photoreceptor 10 provided for image forming apparatus 5 contains the organic photoconductive material of the present invention, represented by the above general formula (1), or specifically by (2), as a charge transport material, it presents a high electrified potential, high sensitivity and high enough light response, and is excellent in durability and will not degrade in these characteristics even in use under a low-temperature environment or in a high-speed process.

Accordingly, it is possible to realize a highly reliable image forming apparatus which can provide high-quality images under various environments. Further, since electrophotographic photoreceptor 10 will not lower its performance by exposure to light, it is possible to eliminate image degradation due to exposure of the photoreceptor to light during maintenance and the like, hence improve the image forming apparatus's reliability.

Next, the present invention will be described in further detail with reference to the embodiments. However, the present invention should not be limited to these.

PREPARATION EXAMPLE 1

Preparation of Example Compound No. 28

Preparation Example 1-1

Preparation of Enamine Intermediate

Added to 100 ml toluene are 21.9 g (1.0 equivalent) of N-phenyl-α-naphtylamine, represented by the following structural formula (8), 20.6 g (1.05 equivalents) of diphenyl acetaldehyde, and 0.23 g (0.01 equivalent) of DL-10-camphor sulfonic acid, and the mixture is heated to react for 6 hours while water as a byproduct was removed out of the system as an azeotrope with toluene. After the end of the reaction, the reaction solution was condensed to about one tenth (1/10) the volume, and then slowly dropped into an intensively stirred 100 ml volume of hexane so as to become crystalline. The resultant crystals were filtered off and washed with cold ethanol. As a result, a light yellow powdery compound in an amount of 34.9 g was obtained.

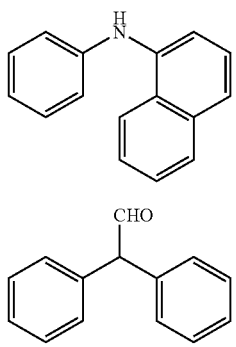

(8)

(9)

The resultant compound was analyzed by the liquid chromatography-mass spectrometry (abbreviation: LC-MS) analysis, and a peak at 398.4, which corresponds to a molecular ion [M+H]$^+$, that is, the enamine intermediate (calculated molecular weight: 397.18), represented by the following structural formula (10), to which a proton is joined, was observed. From this result, the obtained compound was known to be the enamine intermediate represented by the following structural formula (10) (yield: 88%). From the LC-MS analysis, the resultant enamine intermediate was found to have a purity of 99.1%.

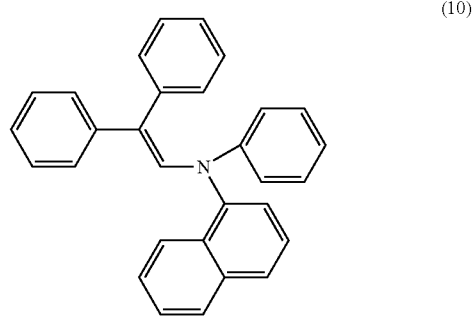

(10)

As above, the enamine intermediate represented by the above structural formula (10) could be obtained by implementing a dehydration and condensation reaction between N-(p-tolyl)-α-naphtylamine, a secondary amine compound represented by the following structural formula (8), and diphenyl acetaldehyde, an aldehyde compound represented by the above structural formula (9).

Preparation Example 1-2

Preparation of Enamine-bis-aldehyde Intermediate

Phosphorus oxichloride in an amount of 18.4 g (2.4 equivalents) was slowly added to 100 ml anhydrous N,N-dimethylformamide (DMF) while being cooled with ice, and stirred for about 30 minutes to prepare a Vilsmeier reagent. The enamine intermediate, obtained by the preparation example 1-1 and represented by the above structural formula (10) in an amount of 19.9 g (1.0 equivalent) was slowly added to this solution while being cooled with ice. Then, the solution was slowly heated to 110 deg. C. for reaction and stirred for 3 hours while being continuously heated to keep 110 deg. C. After the end of the reaction, this reaction solution was left to cool. Then the solution was slowly added to a cooled, 4 normal (4N) 800 ml sodium hydroxide solution so that a precipitate was formed. The obtained precipitate was filtered off, sufficiently washed with water, and then re-crystallized from a solvent mixture of ethanol and ethyl acetate. As a result, a yellow powdery compound in an amount of 19.2 g was obtained.

From the result of an LC-MS analysis of the obtained compound, a peak at 454.1, which corresponds to a molecular ion [M+H]$^+$, that is, the enamine-bis-aldehyde intermediate (calculated molecular weight: 453.17), represented by the following structural formula (11), to which a proton is joined, was observed. From this result, the obtained compound was known to be the enamine-aldehyde intermediate represented by the following structural formula (11) (yield: 85%). From the LC-MS analysis, the resultant enamine-aldehyde intermediate was found to have a purity of 99.2%.

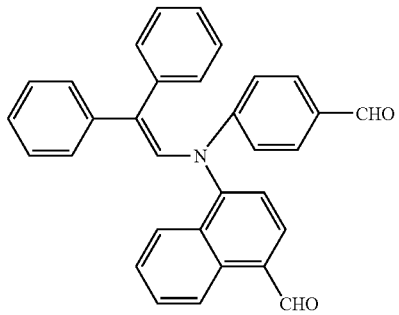

(11)

As above, the enamine-bis-aldehyde intermediate represented by the above structural formula (11) could be obtained by formylating the enamine intermediate represented by the above structural formula (10) based on the Vilsmeier reaction.

Preparation Example 1-3

Preparation of Example Compound No. 28

The enamine-aldehyde intermediate represented by the above structural formula (11), obtained by preparation example 1-2, in an amount of 9.08 g (1.0 equivalent) and diethylcinnamyl phosphonate represented by the following structural formula (12) in an amount of 12.2 g (2.4 equivalents) were dissolved in 80 ml anhydride DMF. Then, 5.6 g (2.5 equivalents) potassium t-butoxide was slowly added to this solution at 0 deg. C. Thereafter, the solution was left for one hour at room temperature, then heated to 50 deg. C. and stirred for 5 hours while being heated to keep 50 deg. C. The reaction mixture was left to cool and then poured into excessive methanol. The precipitate was collected and dissolved into toluene, forming a toluene solution. This toluene solution was poured to a separating funnel. After washing with water, an organic layer was extracted. The extracted organic layer was dried with magnesium sulfate. After drying, the organic layer from which solid matter was removed was condensed and then processed by implementing silicagel column chromatography. As a result, yellow crystals in an amount of 11.7 g was obtained.

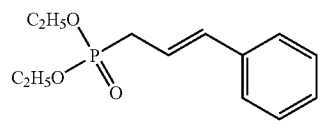

(12)

The obtained crystals were analyzed by LC-MS. As a result, a peak at 654.2, which corresponds to a molecular ion [M+H]$^+$, that is, the aiming enamine compound shown as example compound No. 28 in Table 6, (calculated molecular weight: 653.31), to which a proton is jointed, was observed.

Further, the nuclear magnetic resonance (abbreviation: NMR) spectrum of the obtained crystals in heavy hydrogenchloroform (chemical formula: CDCl$_3$) was measured. As a result, a spectrum backing up the enamine compound structure of example compound No. 28 was obtained.

Figure 5:
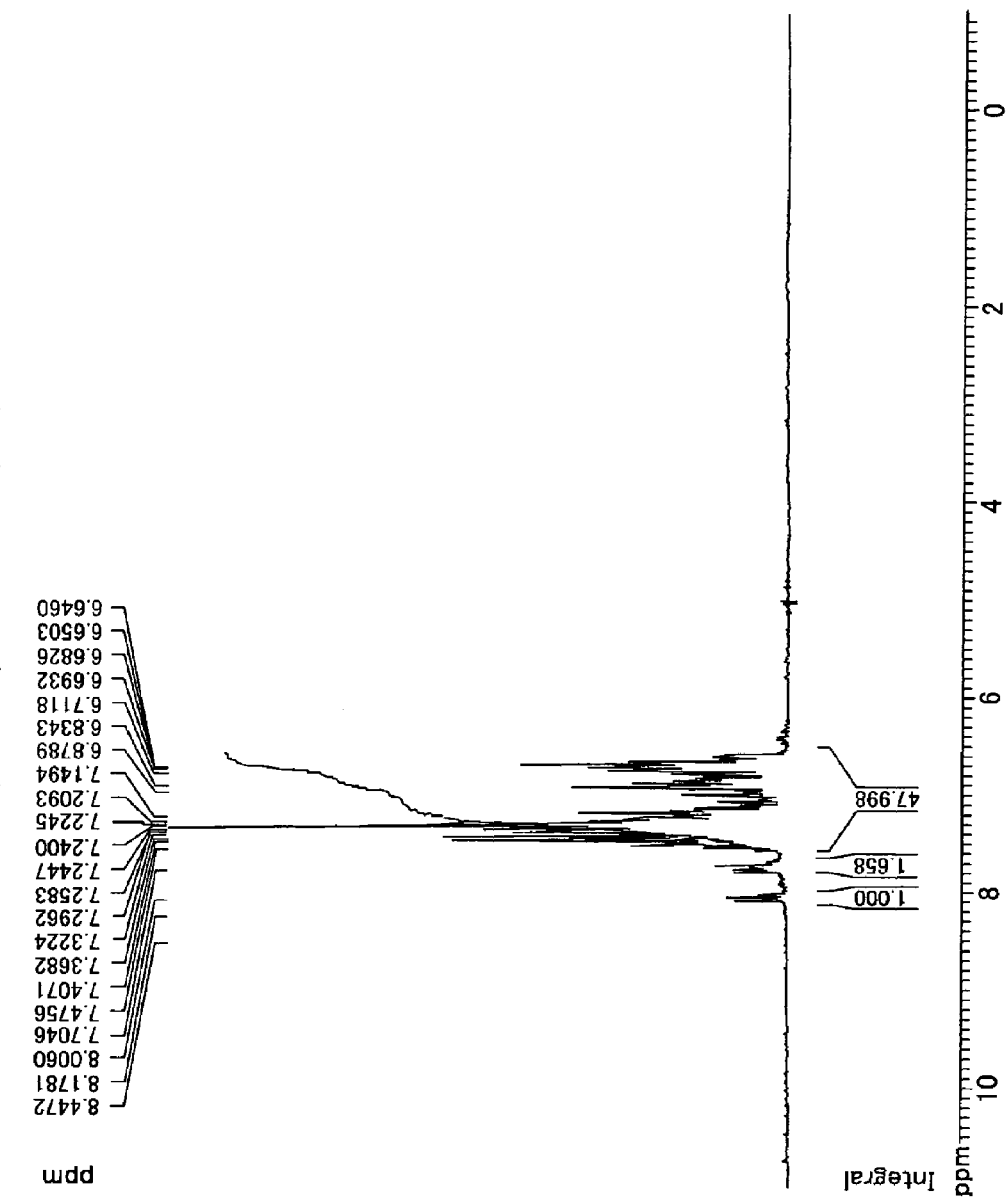
FIG. 5 is a chart showing a $^1$H-NMR spectrum of an example compound No. 28(1-1) of the present embodiment.
Figure 6:
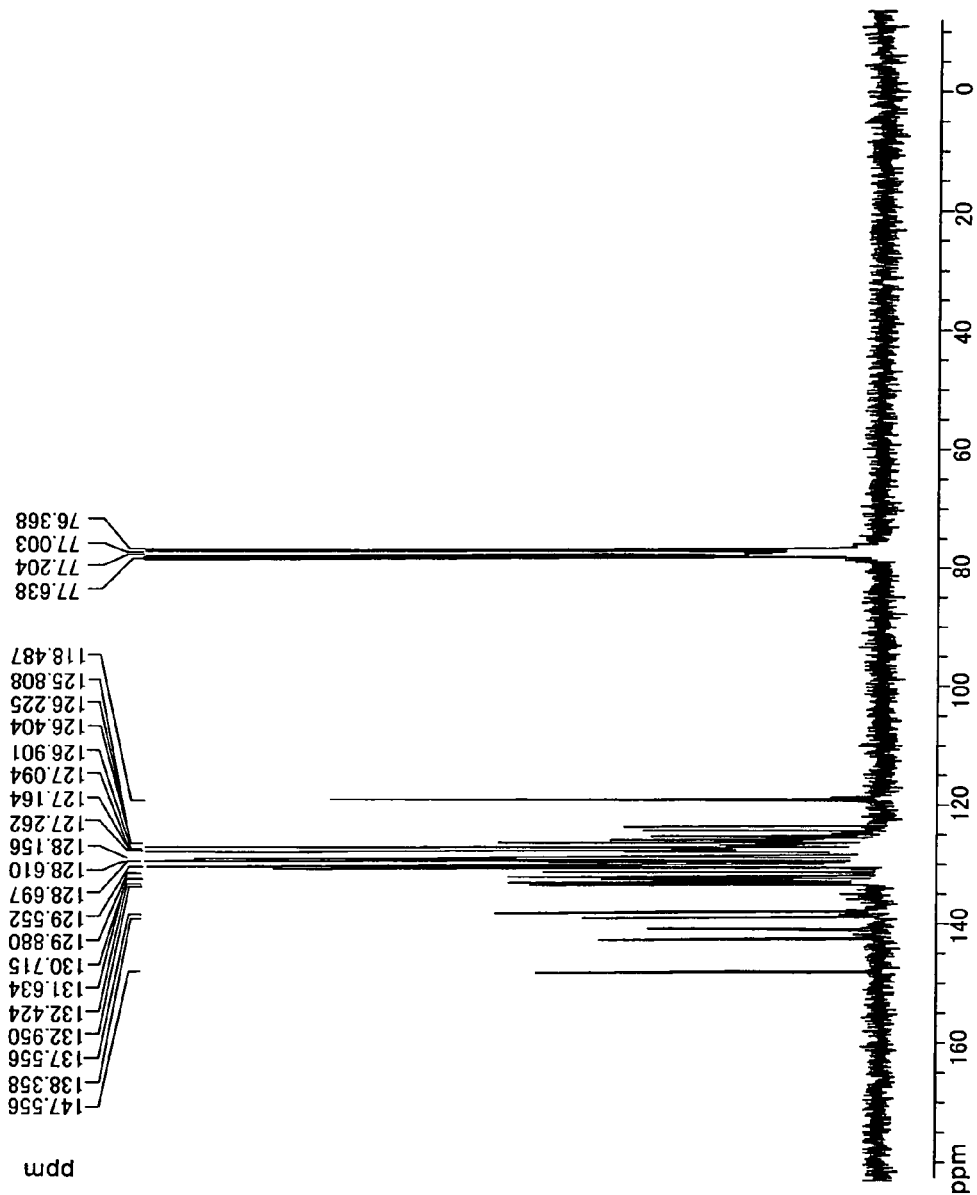
FIG. 6 is a chart showing a $^{13}$C-NMR spectrum, by normal measurement, of an example compound No. 28(1-1) of the present embodiment.

FIG. 5 is a chart showing a $^1$H-NMR spectrum of a product of preparation example 1-3; FIG. 6 is a chart showing a $^{13}$C-NMR spectrum of a product of preparation example 1-3, by normal measurement; and FIG. 7 is a chart showing a $^{13}$C-NMR spectrum of a product of preparation example 1-3, measured by DEPT135.

Figure 7:
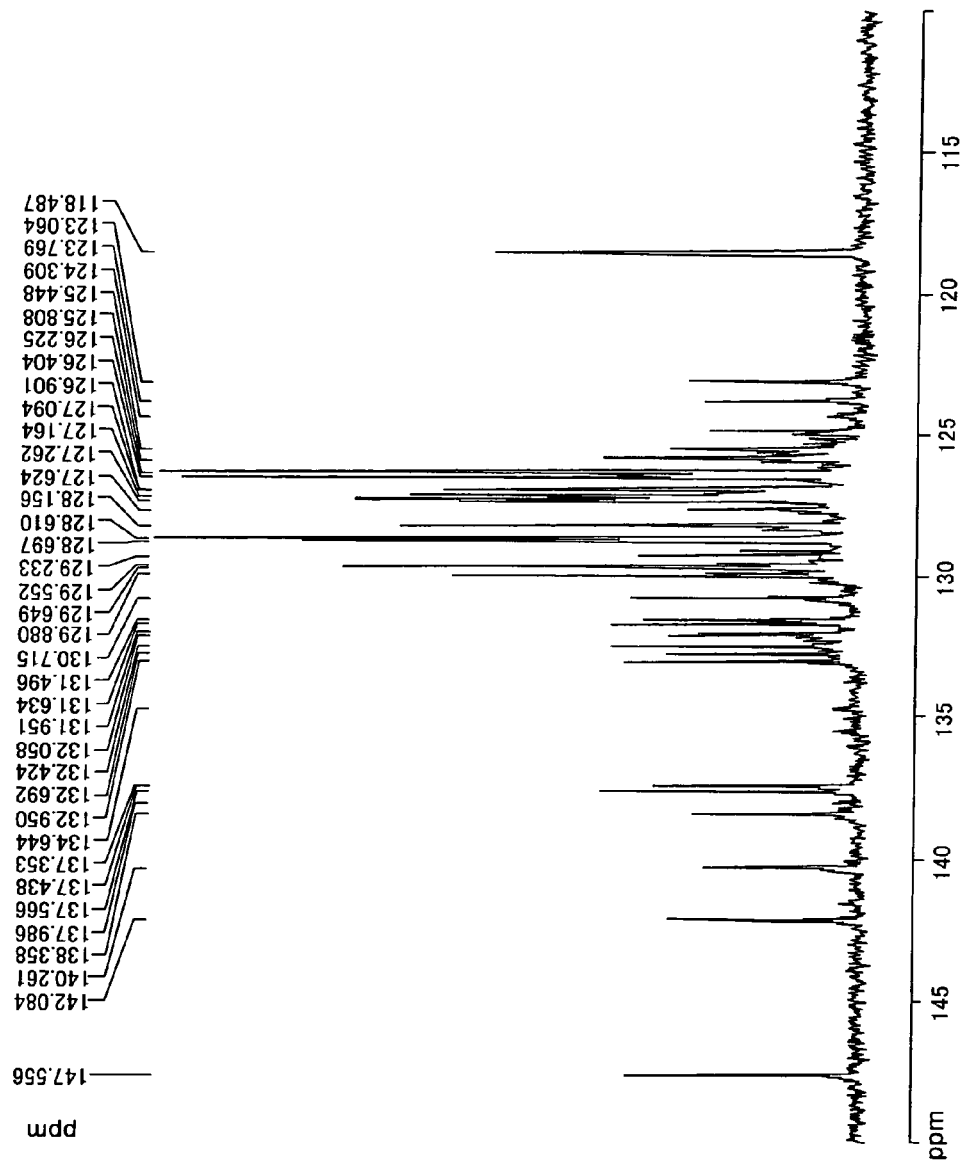
FIG. 7 is a chart showing the enlarged spectrum from 110 ppm to 150 ppm of the chart shown in FIG. 6.

In FIGS. 5 to 7, the horizontal axis denotes the chemical shift value δ (ppm). In FIG. 5, the numerical values written between the signal and horizontal axis are the relative integrations of associated signals.

From the LC-MS analysis result and the NMR spectrum measurement result, the obtained crystals were found to be an enamine compound corresponding to example compound No. 28 (yield: 90%). From the LC-MS analysis result, the obtained enamine compound corresponding to example compound No. 28 was found to have a purity of 99.7%.

As above, the enamine compound represented as example compound No. 28 in Table 6 could be obtained by implementing a Wittig-Horner reaction between the enamine aldehyde intermediate represented by the above structural formula (11) and diethylcinnamyl phosphonate as a Wittig reagent represented by the above structural formula (12).

PREPARATION EXAMPLE 2

Preparation of Example Compound No. 60

This was prepared in the same manner as Preparation Example 1, except in that 4.59 g (1.0 equivalent) of N-(m-tolyl)-α-naphtylamine was used instead of 23.3 g (1.0 equivalent) N-phenyl-α-naphtylamine, represented by the above structural formula (8), an enamine intermediate was prepared (yield: 89%) by a dehydration and condensation reaction, an enamine aldehyde intermediate was prepared (yield: 82%) by the Vilsmeier reaction, and further the Wittig-Horner reaction was done to produce a yellow powdery compound in an amount of 7.67 g. The relationship between the equivalent of the reagent and that of the basic substances used for each reaction was the same as the relationship between the equivalent of the reagent and that of the basic substances used in Preparation Example 1.

The resultant compound was analyzed by LC-MS. As a result, a peak at 668.1, which corresponds to a molecular ion [M+H]$^+$, that is, the aiming enamine compound shown as example compound No. 60 in Table 1, (calculated molecular weight: 667.32), to which a proton is jointed, was observed.

From the result of the LC-MS analysis, the resultant compound was found to be an enamine compound corresponding to example compound No. 60 and have a purity of 99.1%.

As above, use of the three steps of reactions including the dehydration and condensation reaction, the Vilsmeier reaction and the Wittig-Horner reaction, made it possible to provide an enamine compound corresponding to example compound No. 60 shown in the table, with a yield of 58.4% for the three steps of reactions.

PREPARATION EXAMPLE 3

Preparation of Example Compound No. 46

The enamine-bis-aldehyde intermediate represented by the above structural formula (11), obtained by preparation example 1-2, in an amount of 2.06 g (1.0 equivalent) and a Wittig reagent represented by the following structure formula (13) in an amount of 3.06 g (2.4 equivalents) were dissolved in 15 ml anhydride DMF. Then, 1.42 g (2.5 equivalents) potassium t-butoxide was slowly added to that solution at 0 deg. C. Thereafter, the solution was left for one hour at room temperature, then heated to 50 deg. C. and stirred for 5 hours while being heated to keep 50 deg. C. The reaction mixture was left to cool and then poured into excessive methanol. The precipitate was collected and dissolved into toluene, forming a toluene solution. This toluene solution was poured to a separating funnel. After washing with water, an organic layer was extracted. The extracted organic layer was dried with magnesium sulfate. After drying, the organic layer from which solid matter was removed was condensed and then processed by implementing silicagel column chromatography. From this, yellow crystals in an amount of 2.69 g were obtained.

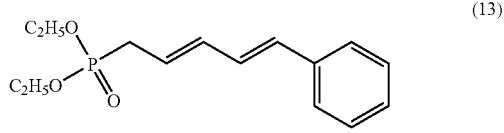

(13)

The obtained crystals were analyzed by LC-MS. As a result, a peak at 706.2, which corresponds to a molecular ion [M+H]$^+$, that is, the aiming enamine compound shown as example compound No. 46 in Table 10, (calculated molecular weight: 705.34), to which a proton is jointed, was observed. From this observation, the obtained crystals were found to be the enamine compound of example compound No. 46 (yield: 84%). From the LC-MS analysis result, the obtained enamine compound corresponding to example compound No. 46 was found to have a purity of 99.8%.

As above, the enamine aldehyde intermediate of example compound No. 46 in Table 10 could be obtained by implementing a Wittig-Horner reaction between the enamine aldehyde intermediate represented by the above structural formula (11) and the Wittig reagent represented by the above structural formula (13).

COMPARATIVE PREPARATION EXAMPLE 1

Preparation of a Compound Represented by the Following Structural Formula (14)

The enamine-bis-aldehyde intermediate represented by the above structural formula (11), obtained by preparation example 1-2, in an amount of 2.0 g (1.0 equivalent) was dissolved in 15 ml an hydride THF. Then, a 10.5 ml THF solution (molarity: 1.0 mol/l) of aryl magnesium bromide (2.3 equivalents) as a Grignard reagent, prepared from aryl bromide and metal magnesium, was slowly added to the above solution at 0 deg. C. After a stirring for 0.5 hour at 0 deg. C., the progress of the reaction was examined by thin layer chromatography. From this examination, no distinct reaction product was recognized while multiple products were observed. After a post treatment, extraction and condensation were done by usual method, the reaction mixture was separated and purified by implementing silicagel column chromatography.

However, no aiming compound represented by the following structural formula (14) could be obtained.

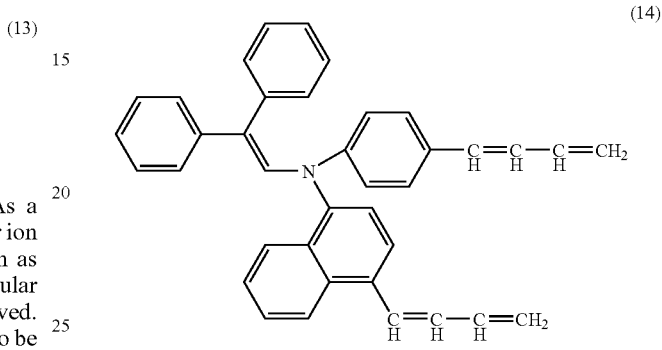

(14)

Embodiment 1

One part by mass of the azo compound for charge generation material 12, represented by the following structural formula (15) was added to a resin solution composed of 99 parts by mass of THF and 1 part by mass of a phenoxy resin (PKHH, a product of Union Carbide Corporation) dissolved therein. Then, the mixture was dispersed for two hours by a paint shaker to prepare a charge generation layer coating liquid. This charge generation layer coating liquid was applied by a Baker applicator over conductive substrate 11, or the aluminum surface deposited on a polyester film having film thickness of 80 μm, then dried to form a charge generation layer 15 having a film thickness of 0.3 μm.

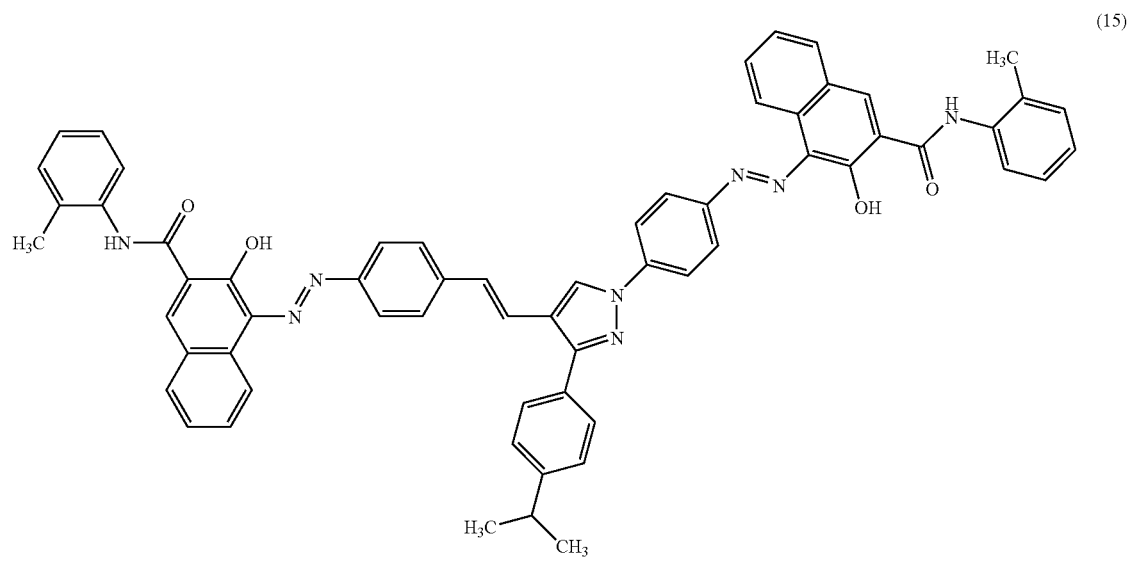

(15)

Next, 8 parts by mass of the enamine compound of example compound No. 28 in Table 6 for charge transport material 13 and 10 parts by mass of a polycarbonate resin (C-1400, a product of Teijin Kasei Corporation) for binder resin 17 were dissolved in 80 parts by mass of THF, to prepare a charge transport layer coating liquid. This charge transport layer coating liquid was applied by a Baker applicator over the previously formed charge generation layer 15, then dried to form a charge transport layer 16 having a film thickness of 10 μm.

The laminated type electrophotographic photoreceptor shown in FIG. 1 was produced in the above manner.

Embodiments 2 to 6

Five types of electrophotographic photoreceptors were produced in the same manner as in embodiment 1, except in that the enamine compound of example compound No. 5, 30, 39 or 46 shown in the tables was used as charge transport material 13 instead of example compound No. 28.

COMPARATIVE EXAMPLE 1

An electro was produced in the same manner as in embodiment 1, except in that a comparative compound A represented by the following structural formula (16) was used as charge transport material 13 instead of example compound No. 28.

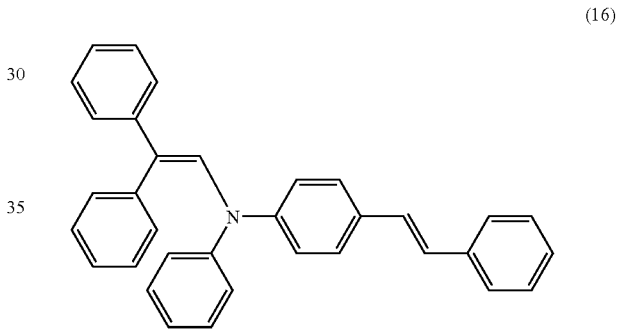

COMPARATIVE EXAMPLE 2

An electrophotographic photoreceptor was produced in the same manner as in embodiment 1, except in that a comparative compound B represented by the following structural formula (17) was used for charge transport material 13 instead of example compound No. 28.

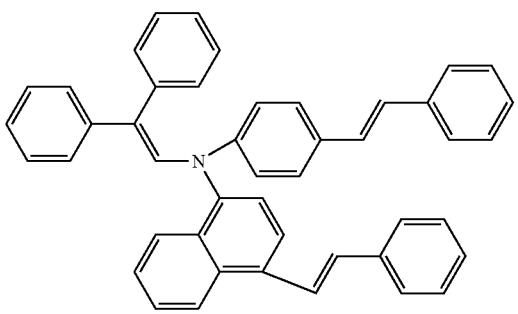

COMPARATIVE EXAMPLE 3

An electrophotographic photoreceptor was produced in the same manner as in embodiment 1, except in that a comparative compound C represented by the following structural formula (18) was used as charge transport material 13 instead of example compound No. 28. (This sample, however, presented countless micro crystals on the sheet surface after film forming and drying, due to poor compatibility of comparative compound C, so that it was impossible to make satisfactory evaluation on the electric characteristics.

(18)

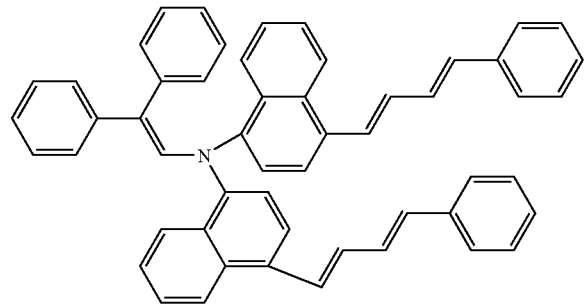

COMPARATIVE EXAMPLE 4

An electrophotographic photoreceptor was produced in the same manner as in embodiment 1, except in that a comparative compound D represented by the following structural formula (19) was used as charge transport material 13 instead of example compound No. 28.

(19)

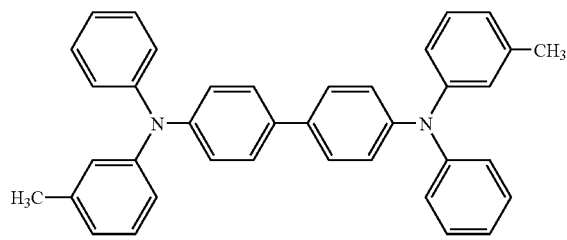

[Evaluation 1]

The ionization potential was measured using a surface analyzer (AC-1, a product of RIKEN KEIKI CO., LTD.) for the electrophotographic photoreceptors produced in the above embodiments 1 to 6 and comparative examples 1 to 4. Further, gold was deposited over the photosensitive layer surface of each electrophotographic photoreceptor, and the charge mobility of charge transport material 13 of each photoreceptor was measured at room temperature under a reduced pressure by the time-of-flight technique. Table 17 shows the measurement result. The charge mobility values shown in Table 17 are the measurements when the electric field strength was set at $2.5 \times 10^5$ V/cm.

TABLE 17

| | Charge transport material | Ionization potential (eV) | Mobility ($cm^2$/V * sec) |
|---|---|---|---|
| Embodiment 1 | Example compound 1 | 5.58 | $5.2 \times 10^{-4}$ |
| Embodiment 2 | Example compound 5 | 5.57 | $6.3 \times 10^{-4}$ |
| Embodiment 3 | Example compound 30 | 5.60 | $7.1 \times 10^{-4}$ |
| Embodiment 4 | Example compound 39 | 5.58 | $6.2 \times 10^{-4}$ |
| Embodiment 5 | Example compound 46 | 5.61 | $5.5 \times 10^{-4}$ |
| Embodiment 6 | Example compound 61 | 5.62 | $6.3 \times 10^{-4}$ |
| Comp. Ex. 1 | Comp. Compound A | 5.63 | $2.0 \times 10^{-5}$ |
| Comp. Ex. 2 | Comp. Compound B | 5.64 | $8.7 \times 10^{-5}$ |
| Comp. Ex. 3 | Comp. Compound C | Exact measurement was impossible due to micro crystals on the sheet surface | |
| Comp. Ex. 4 | Comp. Compound D | 5.40 | $1.2 \times 10^{-6}$ |

From comparison between embodiments 1 to 6 and comparative examples 1, 2 and 4, the organic photoconductive materials of the present invention, represented by the above general formula (1) turned out to present a charge mobility two orders of magnitude higher than that of the enamine styryl compounds such as comparative compounds A and B and triphenylamine dimer (abbreviation: TPD) such as comparative compound D, as the conventionally known charge transport materials. Further, highly symmetrical comparative compound C, namely, enamine bisbutadiene compound, presented countless micro crystals on the sheet surface due to its poor compatibility, hence could not be fully evaluated on its electric characteristics.

Embodiment 7

Nine parts by mass of branch-like titanium oxide (TTO-D-1, a product of Ishihara Industry Co., Ltd.) that has been surface treated by aluminum oxide (chemical formula: $Al_2O_3$) and zirconium dioxide (chemical formula: $ZrO_2$) and 9 parts by mass of copolymer nylon resin (CM8000, a product of Toray Industries, Inc.) were added to a mixture solvent consisting of 41 parts by mass of 1,3-dioxolane and 41 part by mass of methanol. Then, the mixture was dispersed for twelve hours by a paint shaker to prepare an intermediate layer coating liquid. The prepared intermediate layer coating liquid was applied by a Baker applicator over an aluminum substrate of 0.2 mm thick as conductive substrate 11, then dried to form an intermediate layer 18 having a film thickness of 1 μm.

Subsequently, 2 parts by mass of the azo compound for charge generation material 12, represented by the following structural formula (20) was added to a resin solution composed of 97 parts by mass of THF and 1 part by mass of polyvinyl butyral resin (BX-1, a product of SEKISUI CHEMICAL CO., LTD.) dissolved therein. Then, the mixture was dispersed for ten hours by a paint shaker to prepare a charge generation layer coating liquid. This charge generation layer coating liquid was applied by a Baker applicator over the previously formed intermediate layer 18, then dried to form a charge generation layer 15 having a film thickness of 0.3 μm.

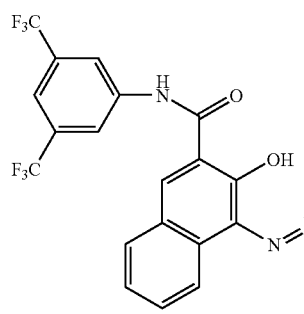
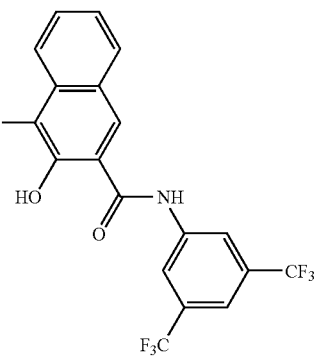

(20)

Next, 10 parts by mass of the enamine compound of example compound No. 28 in Table 6 for charge transport material 13, 14 parts by mass of a polycarbonate resin (Z200, a product of MITSUBISHI GAS CHEMICAL COMPANY, INC.) for binder resin 17 and 0.2 part by mass of 2,6-di-t-butyl-4-methylphenol were dissolved in 80 parts by mass of THF, to prepare a charge transport layer coating liquid. This charge transport layer coating liquid was applied by a Baker applicator over the previously formed charge generation layer 15, then dried to form a charge transport layer 16 having a film thickness of 18 μm.

Thus, a laminated type electrophotographic photoreceptor having a configuration shown in FIG. 2 was produced.

Embodiments 8 to 12

Five types of electrophotographic photoreceptors were produced in the same manner as in embodiment 7, except in that the enamine compound of example compound No. 5, 16, 18, 29 or 47 shown in the tables was used for charge transport material 13 instead of example compound No. 28.

COMPARATIVE EXAMPLES 5 AND 6

Two types of electrophotographic photoreceptors were produced in the same manner as in embodiment 7, except in that a comparative compound A represented by the above structural formula (16) or a comparative compound D represented by the above structural formula (19) was used for charge transport material 13 instead of example compound No. 28.

Embodiment 13

An intermediate layer coating liquid was prepared in the same manner as in embodiment 7. This was applied over an aluminum substrate of 0.2 mm thick as conductive substrate 11, then dried to form an intermediate layer 18 having film thickness of 1 μm.

Subsequently, 1 part by mass of the azo compound for charge generation material 12, represented by the above structural formula (20), 12 parts by mass of a polycarbonate resin (Z-400, a product of MITSUBISHI GAS CHEMICAL COMPANY, INC.) for binder resin 17, 10 parts by mass of the enamine compound of example compound No. 28 in Table 6 for charge transport material 13, 5 parts by mass of 3,5-dimethyl-3',5'-di-t-butyl diphenoquinone, 0.5 part by mass of 2,6-di-t-butyl-4-methylphenol and 65 parts by mass of THF were dispersed by a ball mill to prepare a photosensitive layer coating liquid. The prepared photosensitive layer coating liquid was applied by a Baker applicator over the previously formed intermediate layer 18, then hot-air dried at 110 deg. C. for one hour to form a photosensitive layer 14 having a film thickness of 20 μm as shown in FIG. 3.

Thus, a single-laminated type electrophotographic photoreceptor having a configuration shown in FIG. 3 was produced.

Embodiment 14

An electrophotographic photoreceptor was produced in the same manner as in embodiment 7, except in that X-type metal-free phthalocyanine was used for charge generation material 12 instead of the azo compound represented by the above structural formula (20).

Embodiments 15 to 19

Five types of electrophotographic photoreceptors were produced in the same manner as in embodiment 7, except in that X-type metal-free phthalocyanine was used for charge generation material 12 instead of the azo compound represented by the above structural formula (20), and that the enamine compound of example compound No. 2, 24, 36, 72 or 79 shown in Tables 1 to 16 was used for charge transport material 13 instead of example compound No. 28.

COMPARATIVE EXAMPLES 7 AND 8

Two types of electrophotographic photoreceptors were produced in the same manner as in embodiment 7, except in that X-type metal-free phthalocyanine was used for charge generation material 12 instead of the azo compound represented by the above structural formula (20), and that a comparative compound A represented by the above structural formula (16) or a comparative compound D represented by the above structural formula (19) was used for charge transport material 13 instead of example compound No. 28.

[Evaluation 2]

The electrophotographic photoreceptors produced in the above embodiments 7 to 19 and comparative examples 5-8 were each evaluated on the initial characteristics and repetition characteristics, using an electrostatic copy paper tester (EPA-8200, a product of Kawaguchi Electric Works Co., Ltd.). The tests for evaluation on the initial characteristics and repetition characteristics were carried out under a normal temperature/normal humidity environment, or at a temperature of 22 deg. C., a relative humidity of 65% (22 deg. C./65% RH, to be referred as under N/N environment, hereinafter) and under a low temperature/low humidity environment, or at a temperature of 5 deg. C., a relative humidity of 20% (5 deg. C./20% RH, to be referred as under L/L environment, hereinafter).

Evaluation on the initial characteristics was made in the following manner. The photoreceptor surface was charged by applying a negative voltage, specifically, −5 KV to the photoreceptor and the surface potential of the photoreceptor at this moment was measured as an electrified potential $V_0$ (V). Only for the case of the single layered photoreceptor of embodiment 13, a positive voltage, +5 KV was applied. Then the charged photoreceptor surface was exposed to light. The energy that at this moment was spent to reduce the photoreceptor surface potential from electrified potential $V_0$ (V) to half was measured as a halved-potential energy-of-exposure $E_{1/2}$ (μJ/cm$^2$) and adopted as an evaluation indicator for sensitivity. Further, the photoreceptor surface potential at a point of time after a lapse of 10 second from the start of exposure was measured as a residual potential $V_r$ (V) and was adopted as an evaluation indicator for light response. For light exposure, a white light having an exposure light energy of 1 μW/cm$^2$ was used for the photoreceptors using charge generation material 12 of the azo compound represented by the above structural formula (20) in embodiments 7 to 13 and comparative examples 5 and 6. For the photoreceptors of embodiments 14 to 19 and comparative examples 7 and 8 using X-type metal-free phthalocyanine, a light with a wavelength of 780 nm and an exposure light energy of 1 μW/cm$^2$, which was separated by a monochromator was used.

Evaluation on the repetition characteristics was made in the following manner. After 5,000 of cycles, each cycle being made up of the aforementioned charging and exposure operations, the halved-potential energy-of-exposure $E_{1/2}$, electrified potential $V_0$ and residual potential $V_r$ were measured in the same manner as the evaluation of the initial characteristics.

Table 18-1 and 18-2 shows the above measurement result.

TABLE 18-1

| | | | N/N; 22° C./65% | | | | | |
|---|---|---|---|---|---|---|---|---|
| | | | Initial characteristics | | | Repetition characteristics | | |
| | Charge generation material | Charge transport material | $E_{1/2}$ (mJ/cm$^2$) | $V_0$ (V) | $V_r$ (V) | $E_{1/2}$ (mJ/cm$^2$) | $V_0$ (V) | $V_r$ (V) |
| Embo. 7 | Azo compound(20) | EX. compound 1 | 0.15 | −578 | −18 | 0.19 | −571 | −23 |
| Embo. 8 | Azo compound(20) | EX. compound 5 | 0.16 | −582 | −14 | 0.20 | −574 | −19 |
| Embo. 9 | Azo compound(20) | EX. compound 16 | 0.14 | −577 | −16 | 0.18 | −570 | −21 |
| Embo. 10 | Azo compound(20) | EX. compound 18 | 0.17 | −574 | −13 | 0.19 | −569 | −19 |
| Embo. 11 | Azo compound(20) | EX. compound 29 | 0.16 | −575 | −11 | 0.19 | −570 | −18 |
| Embo. 12 | Azo compound(20) | EX. compound 47 | 0.18 | −580 | −18 | 0.21 | −574 | −26 |
| Com. EX. 5 | Azo compound(20) | Com. compound A | 0.20 | −578 | −35 | 0.22 | −576 | −36 |
| Com. EX. 6 | Azo compound(20) | Com. compound D | 0.21 | −591 | −42 | 0.25 | −589 | −54 |
| Embo. 13 | Azo compound(20) | EX. compound 1 | 0.28 | 555 | 24 | 0.33 | 539 | 33 |
| Embo. 14 | X-type metal-free phthalocyanine | EX. compound 1 | 0.13 | −580 | −8 | 0.15 | −571 | −13 |
| Embo. 15 | X-type metal-free phthalocyanine | EX. compound 2 | 0.14 | −577 | −10 | 0.16 | −570 | −15 |
| Embo. 16 | X-type metal-free phthalocyanine | EX. compound 24 | 0.12 | −581 | −9 | 0.14 | −575 | −12 |
| Embo. 17 | X-type metal-free phthalocyanine | EX. compound 36 | 0.13 | −583 | −12 | 0.16 | −576 | −17 |
| Embo. 18 | X-type metal-free phthalocyanine | EX. compound 72 | 0.15 | −578 | −11 | 0.17 | −570 | −18 |
| Embo. 19 | X-type metal-free phthalocyanine | EX. compound 79 | 0.14 | −576 | −12 | 0.17 | −569 | −17 |
| Com. EX. 7 | X-type metal-free phthalocyanine | Com. compound A | 0.15 | −586 | −25 | 0.17 | −576 | −27 |
| Com. EX. 8 | X-type metal-free phthalocyanine | Com. compound D | 0.15 | −581 | −30 | 0.19 | −575 | −40 |

TABLE 18-2

| | | | L/L; 5° C./20% | | | | | |
|---|---|---|---|---|---|---|---|---|
| | | | Initial characteristics | | | Repetition characteristics | | |
| | Charge generation material | Charge transport material | $E_{1/2}$ (mJ/cm$^2$) | $V_0$ (V) | $V_r$ (V) | $E_{1/2}$ (mJ/cm$^2$) | $V_0$ (V) | $V_r$ (V) |
| Embo. 7 | Azo compound(20) | EX. compound 1 | 0.16 | −589 | −22 | 0.18 | −584 | −14 |
| Embo. 8 | Azo compound(20) | EX. compound 5 | 0.18 | −584 | −20 | 0.19 | −580 | −23 |
| Embo. 9 | Azo compound(20) | EX. compound 16 | 0.15 | −579 | −19 | 0.16 | −574 | −22 |
| Embo. 10 | Azo compound(20) | EX. compound 18 | 0.19 | −576 | −17 | 0.20 | −574 | −21 |
| Embo. 11 | Azo compound(20) | EX. compound 29 | 0.18 | −577 | −15 | 0.19 | −572 | −20 |
| Embo. 12 | Azo compound(20) | EX. compound 47 | 0.20 | −582 | −21 | 0.21 | −578 | −26 |
| Com. EX. 5 | Azo compound(20) | Com. compound A | 0.42 | −579 | −50 | 0.45 | −571 | −51 |
| Com. EX. 6 | Azo compound(20) | Com. compound D | 0.45 | −581 | −55 | 0.51 | −579 | −65 |
| Embo. 13 | Azo compound(20) | EX. compound 1 | 0.30 | 548 | 28 | 0.31 | 534 | 33 |
| Embo. 14 | X-type metal-free phthalocyanine | EX. compound 1 | 0.14 | −583 | −10 | 0.15 | −579 | −16 |
| Embo. 15 | X-type metal-free phthalocyanine | EX. compound 2 | 0.15 | −578 | −13 | 0.16 | −576 | −19 |
| Embo. 16 | X-type metal-free phthalocyanine | EX. compound 24 | 0.14 | −582 | −12 | 0.15 | −578 | −18 |
| Embo. 17 | X-type metal-free phthalocyanine | EX. compound 36 | 0.14 | −584 | −15 | 0.16 | −574 | −20 |
| Embo. 18 | X-type metal-free phthalocyanine | EX. compound 72 | 0.16 | −579 | −14 | 0.17 | −573 | −21 |

TABLE 18-2-continued

| | | | L/L; 5° C./20% | | | | | |
|---|---|---|---|---|---|---|---|---|
| | | Charge transport | Initial characteristics | | | Repetition characteristics | | |
| | Charge generation material | material | $E_{1/2}$ (mJ/cm$^2$) | $V_0$ (V) | $V_r$ (V) | $E_{1/2}$ (mJ/cm$^2$) | $V_0$ (V) | $V_r$ (V) |
| Embo. 19 | X-type metal-free phthalocyanine | EX. compound 79 | 0.16 | −579 | −16 | 0.18 | −574 | −22 |
| Com. EX. 7 | X-type metal-free phthalocyanine | Com. compound A | 0.36 | −580 | −45 | 0.38 | −578 | −46 |
| Com. EX. 8 | X-type metal-free phthalocyanine | Com. compound D | 0.38 | −579 | −50 | 0.45 | −570 | −59 |

From comparison between embodiments 7 to 12 and comparative examples 5 and 6 and from comparison between embodiments 14 to 19 and comparative examples 7 and 8, the photoreceptors of embodiments 7 to 12 and 14 to 19 which use charge transport material 13 of the organic photoconductive materials of the present invention, represented by the above general formula (1) turned out to have a higher sensitivity and an excellent light response due to presentation of a smaller amount of the halved-potential energy-of-exposure $E_{1/2}$ and a smaller residual potential $V_r$ with respect to the negative direction or a smaller potential difference of the residual potential $V_r$ from the reference potential than the photoreceptors of comparative examples 5 to 8 using comparative compound A or D for charge transport material 13. It also turned out that the characteristics could be maintained after repeated usage and under the low temperature/low humidity (L/L) environment.

Embodiment 20

Nine parts by mass of branch-like titanium oxide (TTO-D-1, a product of Ishihara Industry Co., Ltd.) that has been surface treated by aluminum oxide (chemical formula: $Al_2O_3$) and zirconium dioxide (chemical formula: $ZrO_2$) and 9 parts by mass of copolymer nylon resin (CM8000, a product of Toray Industries, Inc.) were added to a mixture solvent consisting of 41 parts by mass of 1,3-dioxolane and 41 part by mass of methanol. Then, the mixture was dispersed for eight hours by a paint shaker to prepare an intermediate layer coating liquid. This intermediate layer coating liquid was poured into the coating bath, and a cylindrical conductive substrate 11 of aluminum having a diameter of 40 mm and a full-length of 340 mm was immersed into the coating bath and drawn up to form an intermediate layer 18 having a film thickness of 1.0 μm on conductive substrate 11.

Subsequently, 2 parts by mass of oxotitanium phthalocyanine that has a crystal structure at least presenting a clear diffraction peak at a Bragg angle (2θ±0.2°) of 27.2° in a X-ray diffraction spectrum with a Cu—Kα characteristic X-ray (wavelength: 1.54 Å), as the oxotitanium phthalocyanine for charge generation material 12, and 1 part by mass of polyvinyl butyral resin (S-LEC BM-S, a product of SEKISUI CHEMICAL CO., LTD.) and 97 parts of methylethyl ketone, were mixed and dispersed by a paint shaker to prepare a charge generation layer coating liquid. This charge generation layer coating liquid was applied over the previously formed intermediate layer 18 in the same manner as for the previously formed intermediate layer 18, or by a dip coating technique to form a charge generation layer 15 having a film thickness of 0.4 μm on intermediate layer 18.

Next, 10 parts by mass of the enamine compound of example compound No. 28 for charge transport material 13, 20 parts by mass of a polycarbonate resin (Iupilon Z200, a product of Mitsubishi Engineering-Plastics Corporation) for binder resin 17, 1 part by mass of 2,6-di-t-butyl-4-methylphenol and 0.004 part by mass of dimethylpolysiloxane (KF-96, a product of Shin-Etsu Chemical Co., Ltd.) were dissolved in 110 parts by mass of tetrahydrofran, to prepare a charge transport layer coating liquid. This charge transport layer coating liquid was applied over the previously formed charge generation layer 15 by the same dip coating technique used for the previously formed intermediate layer 18 and then dried at 110 deg. C. for one hour to form a charge transport layer 16 having a film thickness of 23 μm.

Thus, the electrophotographic photoreceptor was produced.

Embodiments 21 and 22

Two types of electrophotographic photoreceptors were produced in the same manner as in embodiment 20, except in that the enamine compound of example compound No. 1 or 34 shown in Tables 1 and 7 was used for charge transport material 13 instead of example compound No. 28.

COMPARATIVE EXAMPLE 9

An electrophotographic photoreceptor was produced in the same manner as in embodiment 21, except in that a comparative compound A represented by the above structural formula (16) was used for charge transport material 13 instead of example compound No. 28.

Embodiment 23

An electrophotographic photoreceptor was produced in the same manner as in embodiment 20, except in that 25 parts by mass of the polycarbonate resin was used for binder resin 17 of charge transport layer 16.

Embodiments 24 and 25

Two types of electrophotographic photoreceptors were produced in the same manner as in embodiment 20, except in that 25 parts by mass of the polycarbonate resin was used for binder resin 17 of charge transport layer 16, and that the enamine compound of example compound No. 15 or 33 shown in Tables 3 and 7 was used for charge transport material 13 instead of example compound No. 28.

REFERENCE EXAMPLE 1

An electrophotographic photoreceptor was produced in the same manner as in embodiment 20, except in that 10 parts by mass of the polycarbonate resin was used for binder resin 17 of charge transport layer 16.

REFERENCE EXAMPLE 2

An electrophotographic photoreceptor was produced in the same manner as in embodiment 20, except in that 31 parts by mass of the polycarbonate resin was used for binder resin 17 of charge transport layer 16.

Here, charging of the photoreceptor surface was performed by the negative charging process.

Table 19 shows the evaluation result of the above.

TABLE 19

|  | Charge transport material | Charge transport material/ Binder resin | Film reduction $\Delta d$ (μm) | N/N-potential characteristics $V_0$ (V) | $V_L$ (V) | L/L-potential variation $\Delta V_L$ (V) |
|---|---|---|---|---|---|---|
| Embo. 20 | Ex. Comp. 1 | 10/20 | 4.1 | −540 | −38 | −23 |
| Embo. 21 | Ex. Comp. 28 | 10/20 | 4.3 | −530 | −34 | −19 |
| Embo. 22 | Ex. Comp. 34 | 10/20 | 4.2 | −534 | −36 | −24 |
| Comp. Ex. 9 | Com. Ex. A | 10/20 | 4.4 | −518 | −102 | −70 |
| Embo. 23 | Ex. Comp. 1 | 10/25 | 2.9 | −538 | −47 | −29 |
| Embo. 24 | Ex. Comp. 15 | 10/25 | 3.0 | −533 | −45 | −28 |
| Embo. 25 | Ex. Comp. 33 | 10/25 | 3.1 | −532 | −42 | −31 |
| Ref. Ex. 1 | Ex. Comp. 1 | 10/10 | 10.8 | −518 | −17 | −9 |
| Ref. Ex. 2 | Ex. Comp. 1 | 10/31 | — | — | — | — |

However, in forming charge transport layer 16, it was impossible to prepare a charge transport layer coating liquid with the polycarbonate resin completely dissolved in tetrahydrofran of the same amount as that of embodiment 20. Therefore, tetrahydrofran was added to prepare a charge transport layer coating liquid with polycarbonate resin fully dissolved therein, and this was used to form charge transport layer 16.

However, because of an excess of the amount of solvent in the charge transport layer coating liquid, whitening due to brushing occurred at the longitudinal ends of the cylindrical photoreceptor. Therefore, it was impossible to evaluate the characteristics.

[Evaluation 3]

The electrophotographic photoreceptors produced in the above embodiments 20 to 25 and reference example 1 and comparative example 9 were each evaluated on abrasion resistance and electric characteristics stability.

Each of the prepared electrophotographic photoreceptors was set into a digital copier (AR-C150, a product of Sharp Corporation) with its process speed set at 117 mm/sec. After an image forming run of 40,000 sheets, the film thickness d1 of the photosensitive layer was measured, and the difference of this value from the film thickness d0 of the photosensitive layer at production time was determined as a film reduction $\Delta d(=d0-d1)$, which was used as an evaluation indicator of abrasion resistance.

Further, a surface potential meter (CATE751, a product of GEN-TECH, INC.) was arranged inside the copier so as to be able to measure the surface potential of the photoreceptor during the image forming process. Under the N/N environment, specifically, 22 deg. C./65% RH, the surface potential immediately after charging, namely electrified potential $V_0$ (V) and the surface potential immediately after exposure to laser light, namely $V_L$ (V), were measured. Also under the L/L environment, specifically, 5 deg. C./20% RH, the surface potential immediately after exposure to laser light, $V_L$ (V), was measured. Where the surface potential $V_L$, measured under the N/N environment, is denoted as $V_L(1)$, and the surface potential $V_L$, measured under the L/L environment, is denoted as $V_L(2)$, the difference between $V_L(1)$ and $V_L(2)$, i.e., $\Delta V_L(=V_L(2)-V_L(1))$ was determined and used as an evaluation indicator of the stability of electric characteristics.

From comparison between embodiments 20 to 25 and comparative example 9, the photoreceptors of embodiments 21 to 25 which use charge transport material 13 of the organic photoconductive materials of the present invention and reference example 1 turned out to present a smaller value of surface potential $V_L$ under the N/N environment, meaning an excellent light response, even when the binder resin was added at a higher ratio, compared to the photoreceptor of comparative example 9 using comparative compound A. It also turned out that potential variation $\Delta V_L$ was small, meaning that appropriate light response can be obtained also under the L/L environment.

From comparison between embodiments 20 to 25 and comparative example 1, the photoreceptors of embodiments 20 to 25 of which the ratio A/B of the charge transport material (A) and the binder resin (B) ranges from 10/12 to 10/30 turned out to present a smaller film reduction $\Delta d$, meaning a higher abrasion resistance, than the photoreceptor of reference example 1 of which the ratio A/B was 10/10 over 10/12, or the ratio of the binder resin was low.

As above, formation of a charge transport layer containing the organic photoconductive material of the present invention made it possible to improve the abrasion resistance of the charge transport layer without lowering the light response.

As has been described, according to the present invention, since the organic photoconductive material has a specific structure, that is, the substituents of the enamine part are aryl groups or heterocyclic groups and the enamine is also made to form an asymmetrical bis-butadiene or triene structure, it is possible to provide an organic photoconductive material which is excellent in compatibility with binder resins and has high charge mobility free from problems such as deposition of charge transport material during film forming, etc.

Further, according to the present invention, since the organic photoconductive material has a specific structure, it is possible to readily provide an organic photoconductive material having especially high charge mobility.

According to the present invention, since an organic photoconductive material having high mobility is contained as a charge transport material in the photosensitive layer, it is possible to provide a highly reliable electrophotographic photoreceptor which can present a high electrified potential, high sensitivity and high enough light response as well as excellent durability and will not degrade in these characteristics under a low-temperature environment or in a high-speed process and will not lower in these characteristics even due to exposure to light.

According to the present invention, oxotitanium phthalocyanine which is a charge generation material having high charge generation efficiency and charge injection efficiency is contained in the photosensitive layer and it is possible to provide an electrophotographic photoreceptor having a high sensitivity and a high resolution.

According to the present invention, since the photosensitive layer has a layered structure composed of a charge generation layer containing a charge generation material and a charge transport layer containing a charge transport material, it is possible to provide an electrophotographic photoreceptor having a higher sensitivity and an improved stability and higher durability against repeated usage.

Further, according to the present invention, since light response can be maintained even if a higher proportion of binder resin is added to the charge transport material than that in the conventionally known charge transport material, it is possible improve the abrasion resistance of the charge transport layer and the durability of the electrophotographic photoreceptor without lowering the light response.

Further, according to the present invention, since an intermediate layer is provided between a conductive substrate and the photosensitive layer, it is possible to prevent the lowering of the electrification capability of the photosensitive layer hence prevent occurrence of defects such as image fogging etc., as well as to improve the film formability of the photosensitive layer and adhesiveness between the conductive substrate and the photosensitive layer.

Moreover, according to the present invention, since it is possible to obtain a highly reliable electrophotographic photoreceptor which can present a high electrified potential, high sensitivity and high enough light response as well as excellent durability and will not degrade in these characteristics under a low-temperature environment or in a high-speed process and will not lower in these characteristics even due to exposure to light, it is possible to provide an highly reliable image forming apparatus which can present high-quality images under various environments and improve the reliability of the image forming apparatus by preventing the image quality degradation as a result of the photoreceptor being exposed to light during maintenance and the like.

INDUSTRIAL APPLICABILITY

As described heretofore, the organic photoconductive material of the present invention makes it possible to realize a highly reliable electrophotographic photoreceptor which will not present detrimental effects such as partial crystallization at film forming, will present a high electrified potential, a high sensitivity, sufficient light response and excellent durability, will not degrade in these characteristics even when used under a low-temperature environment or in a high-speed process, and will not degrade in these characteristics due to exposure to light, hence present high in industrial applicability. Further, the electrophotographic photoreceptor and image forming apparatus using this organic photoconductive material also present high industrial applicability.

What is claimed is:

1. An organic photoconductive material represented by the following general formula (1):

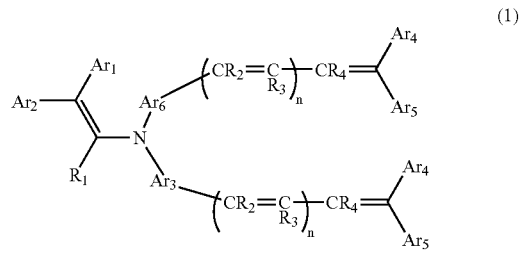

where n is an integer ranging from 0 to 3; $Ar_1$ and $Ar_2$ each represent an aryl group optionally containing a substituent or a heterocyclic group optionally containing a substituent; $Ar_3$ represents a phenylene group optionally containing a substituent and $Ar_6$ represents a naphthylene group optionally containing a substituent; $A_4$ and $Ar_5$ represent one selected from a hydrogen atom, aryl groups optionally containing a substituent, heterocyclic groups optionally containing a substituent, aralkyl groups optionally containing a substituent and alkyl groups optionally containing a substituent, and both $Ar_4$ and $Ar_5$ are not, at the same time, hydrogen atoms, $Ar_4$ and $Ar_5$ may be bonded to each other via an atom or an atomic group, forming a cyclic structure; $R_1$ represents a hydrogen atom, a halogen atom or an alkyl group optionally containing a substituent; and $R_2$, $R_3$ and $R_4$ are selected from a hydrogen atom, alkyl groups optionally containing a substituent, aryl groups optionally containing a substituent, heterocyclic groups optionally containing a substituent and aralkyl groups optionally containing a substituent, and when n is 0, $Ar_3$ represents a heterocyclic group optionally containing a substituent.

2. The organic photoconductive material according to claim 1, wherein the organic photoconductive material represented by the above general formula (1) is one represented by the following general formula (2):

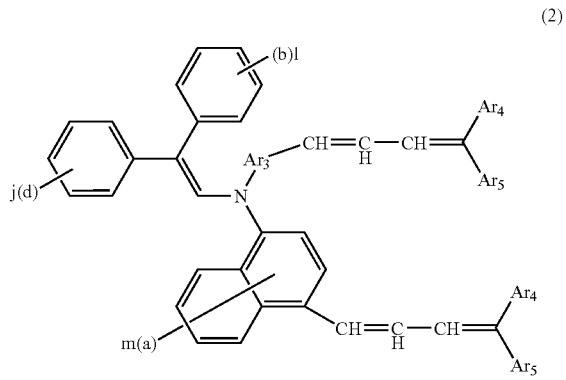

where j and l each are an integer ranging from 1 to 5, m is an integer ranging from 1 to 6; a, b and d each represent one selected from alkyl groups optionally containing a substituent, alkoxy groups optionally containing a substituent, dialkylamino groups optionally containing a substituent, aryl groups optionally containing a substituent and halogen atoms and a hydrogen atom, and when a, b and d each appear in plurality, they may be the same with or different from each other, and also may be joined to each other forming a cyclic structure.

3. An electrophotographic photoreceptor comprising: a conductive substrate consisting of a conductive material; and a photosensitive layer containing a charge generation material and a charge transport material and provided on the conductive substrate, characterized in that the charge transport material contains an organic photoconductive material represented by the following general formula (1):

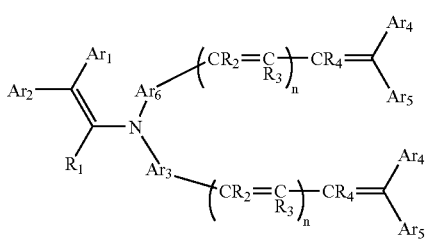

(1)

where n is an integer ranging from 0 to 3; $Ar_1$ and $Ar_2$ each represent an aryl group optionally containing a substituent or a heterocyclic group optionally containing a substituent; $Ar_3$ represents a phenylene group optionally containing a substituent and $Ar_6$ represents a naphthylene group optionally containing a substituent; $A_4$ and $Ar_5$ represent one selected from a hydrogen atom, aryl groups optionally containing a substituent, heterocyclic groups optionally containing a substituent, aralkyl groups optionally containing a substituent and alkyl groups optionally containing a substituent, and both $Ar_4$ and $Ar_5$ are not, at the same time, hydrogen atoms, $Ar_4$ and $Ar_5$ may be bonded to each other via an atom or an atomic group, forming a cyclic structure; $R_1$ represents a hydrogen atom, a halogen atom or an alkyl group optionally containing a substituent; and $R_2$, $R_3$ and $R_4$ are selected from a hydrogen atom, alkyl groups optionally containing a substituent, aryl groups optionally containing a substituent, heterocyclic groups optionally containing a substituent and aralkyl groups optionally containing a substituent, and when n is 0, $Ar_3$ represents a heterocyclic group optionally containing a substituent.

4. The electrophotographic photoreceptor according to claim 3, wherein the organic photoconductive material represented by the above general formula (1) is one represented by the following general formula (2):

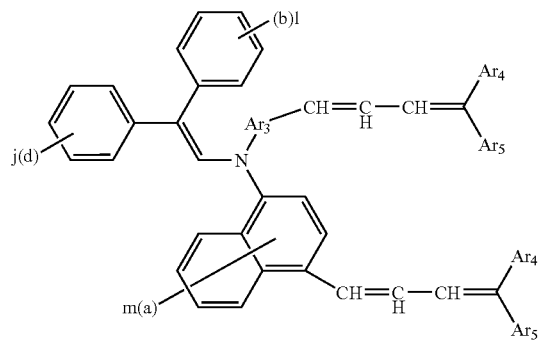

(2)

where j and l each are an integer ranging from 1 to 5, m is an integer ranging from 1 to 6; a, b and d each represent one selected from alkyl groups optionally containing a substituent, alkoxy groups optionally containing a substituent, dialkylamino groups optionally containing a substituent, aryl groups optionally containing a substituent and halogen atoms and a hydrogen atom, and when a, b and d each appear in plurality, they may be the same with or different from each other, and also may be joined to each other forming a cyclic structure.

5. The electrophotographic photoreceptor according to claim 3, wherein the charge generation material contains oxotitanium phthalocyanine that at least presents a clear diffraction peak at a Bragg angle (2θ±0.2°) of 27.2° in a X-ray diffraction spectrum with a Cu—Kα characteristic X-ray (wavelength: 1.54 Å).

6. The electrophotographic photoreceptor according to claim 4, wherein the charge generation material contains oxotitanium phthalocyanine that at least presents a clear diffraction peak at a Bragg angle (2θ±0.2°) of 27.2° in a X-ray diffraction spectrum with a Cu—Kα characteristic X-ray (wavelength: 1.54 Å).

7. The electrophotographic photoreceptor according to claim 3, wherein the photosensitive layer has a layered structure composed of a charge generation layer containing the charge generation material and a charge transport layer containing the charge transport material.

8. The electrophotographic photoreceptor according to claim 7, wherein the charge transport layer further contains a binder resin, and in the charge transport layer the ratio A/B of the charge transport material (A) and the binder resin (B) ranges from 10/12 to 10/30 in mass ratio.

9. The electrophotographic photoreceptor according to claim 3, wherein an intermediate layer is formed between the conductive substrate and the photosensitive layer.

10. An image forming apparatus including an electrophotographic photoreceptor which comprises: a conductive substrate consisting of a conductive material; and a photosensitive layer containing a charge generation material and a charge transport material and provided on the conductive substrate, characterized in that the charge transport material contains an organic photoconductive material represented by the following general formula (1):

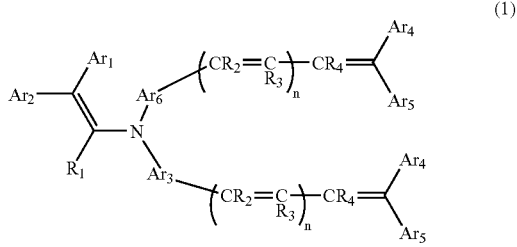

(1)

where n is an integer ranging from 0 to 3; $Ar_1$ and $Ar_2$ each represent an aryl group optionally containing a substituent or a heterocyclic group optionally containing a substituent; $Ar_3$ represents a phenylene group optionally containing a substituent and $Ar_6$ represents a naphthylene group optionally containing a substituent; $A_4$ and $Ar_5$ represent one selected from a hydrogen atom, aryl groups optionally containing a substituent, heterocyclic groups optionally containing a substituent, aralkyl groups optionally containing a substituent and alkyl groups optionally containing a substituent, and both $Ar_4$ and $Ar_5$ are not, at the same time, hydrogen atoms, $Ar_4$ and $Ar_5$ may be bonded to each other via an atom or an atomic group, forming a cyclic structure; $R_1$ represents a hydrogen atom, a halogen atom or an alkyl group optionally containing a substituent; and $R_2$, $R_3$ and $R_4$ are selected from a hydrogen atom, alkyl groups optionally containing a substituent, aryl groups optionally containing a substituent, heterocyclic groups optionally containing a substituent and aralkyl groups optionally containing a substituent, and when n is 0, $Ar_3$ represents a heterocyclic group optionally containing a substituent.

11. The image forming apparatus according to claim 10, wherein the organic photoconductive material represented by the above general formula (1) is one represented by the following general formula (2):

$$\text{(2)}$$

where j and l each are an integer ranging from 1 to 5, m is an integer ranging from 1 to 6; a, b and d each represent one selected from alkyl groups optionally containing a substituent, alkoxy groups optionally containing a substituent, dialkylamino groups optionally containing a substituent, aryl groups optionally containing a substituent and halogen atoms and a hydrogen atom, and when a, b and d each appear in plurality, they may be the same with or different from each other, and also may be joined to each other forming a cyclic structure.

12. The image forming apparatus according to claim 10, wherein the charge generation material contains oxotitanium phthalocyanine that at least presents a clear diffraction peak at a Bragg angle (2θ±0.2°) of 27.2° in a X-ray diffraction spectrum with a Cu—Kα characteristic X-ray (wavelength: 1.54 Å).

13. The image forming apparatus according to claim 11, wherein the charge generation material contains oxotitanium phthalocyanine that at least presents a clear diffraction peak at a Bragg angle (2θ±0.2°) of 27.2° in a X-ray diffraction spectrum with a Cu—Kα characteristic X-ray (wavelength: 1.54 Å).

* * * * *